(12) United States Patent
Kawaoka

(10) Patent No.: US 8,475,806 B2
(45) Date of Patent: Jul. 2, 2013

(54) HIGH TITER RECOMBINANT INFLUENZA VIRUSES FOR VACCINES AND GENE THERAPY

(75) Inventor: Yoshihiro Kawaoka, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/855,875

(22) Filed: May 27, 2004

(65) Prior Publication Data

US 2005/0003349 A1    Jan. 6, 2005

Related U.S. Application Data

(60) Provisional application No. 60/473,798, filed on May 28, 2003.

(51) Int. Cl.
| | | |
|---|---|---|
| A61K 39/12 | (2006.01) | |
| A61K 39/145 | (2006.01) | |
| C12Q 1/70 | (2006.01) | |
| C12P 21/06 | (2006.01) | |
| C12P 21/04 | (2006.01) | |
| C12N 7/00 | (2006.01) | |
| C12N 7/01 | (2006.01) | |
| C12N 15/00 | (2006.01) | |
| C12N 5/10 | (2006.01) | |

(52) U.S. Cl.
USPC .......... 424/206.1; 424/199.1; 424/204.1; 424/205.1; 435/5; 435/69.1; 435/70.1; 435/235.1; 435/320.1; 435/325

(58) Field of Classification Search
USPC ..... 435/320.1, 5, 91.1, 69.1, 209.1; 424/93.2, 424/204.1, 209.1, 186.1
See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 6,033,886 | A | 3/2000 | Conzelmann |
| 6,146,642 | A | 11/2000 | Garcia-Sastre et al. |
| 6,872,395 | B2 | 3/2005 | Kawaoka |
| 2002/0164770 | A1 * | 11/2002 | Hoffmann ............ 435/235.1 |
| 2003/0035814 | A1 | 2/2003 | Kawaoka et al. |
| 2004/0002061 | A1 | 1/2004 | Kawaoka |
| 2004/0219170 | A1 | 11/2004 | Kawaoka |
| 2005/0003349 | A1 | 1/2005 | Kawaoka |
| 2005/0037487 | A1 | 2/2005 | Kawaoka et al. |
| 2006/0166321 | A1 | 7/2006 | Kawaoka et al. |
| 2007/0231348 | A1 * | 10/2007 | Kawaoka et al. ...... 424/209.1 |

FOREIGN PATENT DOCUMENTS

| | | | |
|---|---|---|---|
| EP | 0702085 | A1 | 3/1996 |
| EP | 1 201 760 | A1 * | 2/2002 |
| WO | WO-98/02530 | A1 | 1/1998 |
| WO | WO-98/53078 | A1 | 11/1998 |
| WO | WO-9928445 | A1 | 6/1999 |
| WO | WO-00/60050 | A2 | 10/2000 |
| WO | WO-0060050 | A2 | 10/2000 |
| WO | WO-0060050 | A3 | 10/2000 |
| WO | WO-01/79273 | A2 | 10/2001 |
| WO | WO-03/068923 | A2 | 8/2003 |
| WO | WO-2004/112831 | A2 | 12/2004 |
| WO | WO-2004112831 | A2 | 12/2004 |

OTHER PUBLICATIONS

Result 1, NCBI BLAST nucleotide search of SEQ ID No. 3, database "nr"; Result 4, NCBI BLAST nucleotide search of SEQ ID No. 4, database "nr".*
Result 2, NCBI BLAST nucleotide search of SEQ ID No. 5, database "nr"; Result 4, NCBI BLAST nucleotide search of SEQ ID No. 6, database "nr".*
Schickli et al., "Plasmid-only rescue of influenza A virus vaccine candidates, " Phil. Trans. R. Soc. Lond. B, 356, pp. 1965-1973 (2001).*
Result 1, NCBI BLAST nucleotide search of SEQ ID No. 7, database "nr"; Result 1, NCBI BLAST nucleotide search of SEQ ID No. 8, database "nr".*
Result 17, NCBI BLAST nucleotide search of SEQ ID No. 2, database "nr".*
Smeenk et al., "Mutations in the hemagglutinin and matrix genes of a virulent influenza virus variant, A/FM/1/47-MA, control different stages in pathogenesis," Virus Research 44 (1996) 79-95.*
Result 7, NCBI BLAST nucleotide search of SEQ ID No. 1, database "nr".*
Odagiri et al., Nucleotide sequence of the PA gene of influenza A/WSN/33 (H1N1).*
Chen et al., Generation and evaluation of a high-growth reassortant H9N2 influenza A virus as a pandemic vaccine candidate, 2003, Vaccine, vol. 21, pp. 1974-1979.*
"International Search Report for corresponding PCT Application No. PCT/US2004/016680", (Feb. 2, 2005), 7 pgs.
Fodor, E., "Rescue of Influenza A Virus from Recombinant DNA", *Journal of Virology*, 73(11), (1999), 9679-9682.
Hoffmann, E., et al., "A DNA Transfection System for Generation of Influenza A Virus from Eight Plasmids", *Proceedings of the National Academy of Sciences of USA National Academy of Science USA*, 97 11), (2000), 6108-6113.
Hoffmann, E., et al., "Eight-plasmid System for Rapid Generation of Influenza Virus Vaccines", *Vaccine, Butterworth Scientific Guildford*, 20(25-56), (2002), 3165-3170.
Hoffmann, E., et al., "Rescue of Influenza B Virus from Eight Plasmids", *Proceedings of the National Academy of Sciences of USA, National Academy of Science USA*, 99(17), (2002), 11411-11416.
Neumann, G., "Generation of Influenza A Virus from Cloned cDNAs—Historical Perspective and Outlook for the New Millenium", *Reviews in Medical Virology* 12(1) (2002), 13-30.
Neumann, G., "Generation of Influenza A Viruses Entirely from Cloned cDNAs", *Proceedings of the National Academy of Sciences USA*, 96.(1999),9345-9350.

(Continued)

*Primary Examiner* — Louise Humphrey
(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes a sequence from a high titer influenza virus isolate.

32 Claims, 4 Drawing Sheets

OTHER PUBLICATIONS

Figure 1:
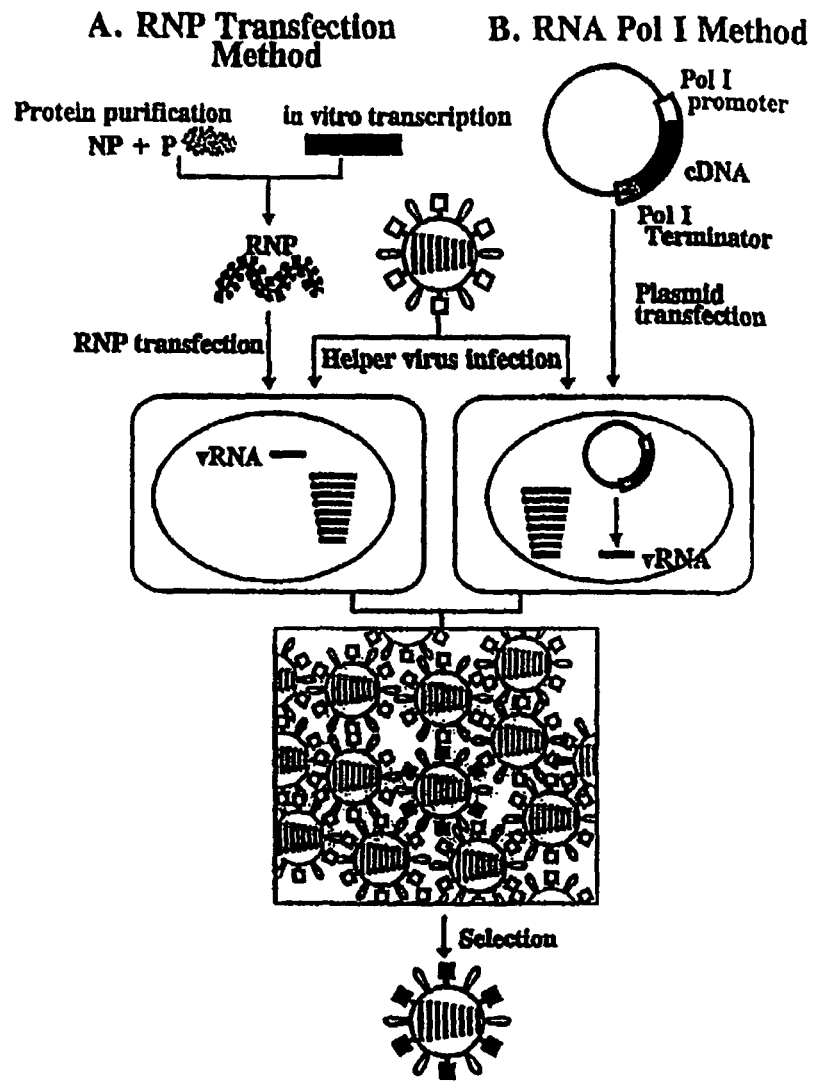

Neumann, G., et al., "Plasmid-Driven Formation of Influenza Virus-like Particles", *Journal of Virology* 74(1), (2000), 547-551.

Schickli, J. H., et al., "Plasmid-only Rescue of Influenza A Virus Vaccine Candidates", *Philosophical Transactions of the Royal Society of London. Series B, Biological Sciences*, 356(1416), (2004), 1965-1973.

Subbarao, K., et al., "Evaluation of a Genetically Modified Reassortant H5N1 Influenza A Virus Vaccine Candidate Generated by Plasmid-based Reverse Genetics", *Virology*, 305(1), (2003), 192-200.

Banerjee, A. K., et al., "Gene Expression of Vesicular Stomatitis Virus Genome RNA.", *Virology*, 188(2), (1992),417-428.

Baron, M. D., et al., "Rescue of Rinderpest Virus From Cloned cDNA", *Journal of Virology*, 71(2), (1997),1265-1271.

Beare, A. S., "Trials in Man With Live Recombinants Made From A/PR/8/34 (H0 N1 and Wild H3 N2 Influenza Viruses", *The Lancet*, 2(7938), (1975),729-732.

Boyer, J.-C., et al., "Infectious Transcripts and cDNA Clones of RNA Viruses", *Virology*, 198 (1994),415-426.

Bridgen, A., et al., "Rescue of a Segmented Negative-Strand RNA Virus Entirely From Cloned Complementary DNAs", *Proc. Natl. Acad. Sci. USA*, 93, (1996),15400-15404.

Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", *Journal of Virology*, 73(1), (1999), 251-259.

Bukreyev, A., et al., "Recovery of Infectious Respiratory Syncytial Virus Expressing an Additional, Foreign Gene", *Journal of Virology*, 70(10)), (1996), 6634-6641.

Castrucci, M., "Reverse Genetics System for Generation of an Influenza A Virus Mutant Containing a Deletion of the Carboxyl-Terminal Residue of M2 protein", *Journal of Virology*, 69(5), (1995),2725-2728.

Chen, Z., et al., "Influenza A Virus NS1 Protein Targets Poly(A)-Binding Protein II of the Cellular 3'-End Processing Machinery", *The EMBO Journal*, 18(8), (1999),2273-2283.

Clarke, D. K., et al., "Rescue of Mumps Virus From cDNA", *Journal of Virology*. 74(10), (2000),4831-4838.

Collins, P. L., et al., "Chapter 41—Parainfluenza Viruses", *In: Fields Virology* Fields, B. N., et al., Editors, Lippincott-Raven Publishers (3rd Edition, 1996) 1205-1241.

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", *Proc. Natl. Acad. Sci. USA*, 92, (1995),11563-11567.

Collins, P. L., "Rescue of Synthetic Analogs of Respiratory Syncytial Virus Genomic RNA and Effect of Truncations and Mutations on the Expression of a Foreign Reporter Gene", *Proc. Natl. Acad. Sci. USA*, 88, (1991),9663-9667.

Conzelmann, K.-K., et al., "Genetic Engineering of Animal RNA Viruses", *Trends in Microbiology*, 4(10), (1996),386-393.

Conzelmann, K.-K., "Genetic Manipulation of Non-Segmented Negative-Strand RNA Viruses", *Journal of General Virology*, 77 (1996),381-389.

Conzelmann, K.-K., "Nonsegmented Negative-Strand RNA Viruses: Genetics and Manipulation of Viral Genomes", *Annu. Rev. Genet.*, 32, (1998),123-162.

Conzelmann, K.-K., et al., "Rescue of Synthetic Genomic RNA Analogs of Rabies Virus by Plasmid-Encoded Proteins", *Journal of Virology*, 68(2), (1994),713-719.

De, B. P., et al., "Requirements and Functions of Vesicular Stomatitis Virus L and NS Proteins in the Transcription Process in Vitro", *Biochemical and Biophysical Research Communications*, 126(1) (1985),40-49.

De, B. P., et al., "Rescue of Synthetic Analogs of Genome RNA of Human Parainfluenza Virus Type 3", *Virology*, 196, (1993),344-348.

De, B. P., et al., "Reverse Genetics of Negative Strand RNA Viruses", *Indian Journal of Biochemist & Biophysics*, 31, (1994),367-375.

De La Luna, S., et al., "Influenza Virus Naked RNA Can Be Expressed Upon Transfection Into Cells Co-Expressing the Three Subunits of the Polymerase and the Nucleoprotein From Simian Virus 40 Recombinant Viruses", *Journal of General Virology*, 74, (1993),535-539.

De La Luna, S., et al., "Influenza Virus NS1 Protein Enhances the Rate of Translation Initiation of Viral mRNAs", *Journal of Virology*, 69(4), (1995),2427-2435.

Dimock, K., et al., "Rescue of Synthetic Analogs of Genomic RNA and Replicative-Intermediate RNA of Human Parainfluenza Virus Type 3", *Journal of Virology*, 67(5), (1993),2772-2778.

Dreher, T. W., et al., "Mutational Analysis of the Sequence and Structural Requirements in Brome Mosaic Virus RNA for Minus Strand Promoter Activity", *Journal of Molecular Biology*, 201(1), (1988),31-40.

Dunn, E. F., et al., "Transcription of a Recombinant Bunyavirus RNA Template by Transiently Expressed Bunyavirus Proteins", *Virology*, 211, (1995),133-143.

Durbin, A. P., et al., "Recovery of Infectious Human Parainfluenza Virus Type 3 From cDNA", *Virology*, 235, (1997),323-332.

Elliott, et al., "Rescue of Infectious Bunyavirus Entirely From Cloned cDNA", *10th International Conference on Negative Strand Virus*, (Abstract No. 96), (1997), 1 pg.

Elliott, R. M., et al., "Some Highlights of Virus Research in 1990", *Journal of General Virology*, 72(Part 8), (1991),1761-1779.

Emerson, S. U., et al., "Both NS and L Proteins Are Required for In Vitro RNA Synthesis by Vesicular Stomatitis Virus", *Journal of Virology*, 15(6), (1975),1348-1356.

Enami, M., et al., "An Influenza Virus Containing Nine Different RNA Segments", *Virology*, 185(1), (1991),291-298.

Enami, M., et al., "High-Efficiency Formation of Influenza Virus Transfectants", *Journal of Virology*, 65(5), (1991),2711-2713.

Enami, M., et al., "Introduction of Site-Specific Mutations Into the Genome of Influenza Virus", *Proc. Natl. Acad. Sci. USA*, 87, (1990),3802-3805.

Fahey, J. L., "Status of Immune-Based Therapies in HIV Infection and Aids", *Clinincal and Experimental Immunology*, 88(1), (1992),1-5.

Fortes, P., et al., "Influenza Virus NS1 Protein Inhibits Pre-mRNA Splicing and Blocks mRNA Nucleocytoplasmic Transport", *The EMBO Journal*, 13(3), (1994),704-712.

Garcia-Sastre, A., et al., "Genetic Manipulation of Negative-Strand RNA Virus Genomes", *Annu. Rev. Microbiol.*. 47, (1993),765-790.

Garcin, D., et al., "A Highly Recombinogenic System for the Recovery of Infectious Sendai Paramyxovirus From cDNA: Generation of a Novel Copy-Back Nondefective Interfering Virus", *The EMBO Journal*, 14(24), (1995),6087-6094.

Goto, H., et al., "Mutations Affecting the Sensitivity of the Influenza Virus Neuraminidase to 4-Guanidino-2, 4-dideoxy 2, 3-dehydro-N-acetylneuraminic Acid", *Virology*, 238, (1997),265-272.

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", *Journal of Virology*, 69(9), (1995),5677-5686.

Hatada, E., et al., "Binding of Influenza A Virus NS1 Protein to dsRNA in vitro", *Journal of General Virology*, 73, 1992 ,3325-3329.

He, B., et al., "Recovery of Infectious SV5 From Cloned DNA and Expression of a Foreign Gene", *Virology*, 237, (1997),249-260.

Hoffman, M. A., et al., "An Infectious Clone of Human Parainfluenza Virus Type 3", *Journal of Virology*, 71(6), (1997),4272-4277.

Hoffmann, E., et al., ""Ambisense" Approach for the Generation of Influenza A Virus: vRNA and mRNA Synthesis from One Template", *Virology*, 267, (2000),310-317.

Huang, T.-S., et al., "Determination of Influenza Virus Proteins Required for Genome Replication", *Journal of Virology*, 64(11), (1990),5669-5673.

Kaplan, G., et al., "In vitro Synthesis of Infectious Poliovirus RNA", *Proc. Natl. Acad. Sci. USA*, 82, (1985),8824-8428.

Katinger, et al., "Attenuated Influenza Viruses as a Vector for Mucosal Immunization Against HIV-1", *Vaccines*, 97, (1997),315-319.

Kato, A., et al., "Initiation of Sendai Virus Multiplication From Transfected cDNA or RNA With Negative or Positive Sense", *Genes to Cells*, 1, (1996),569-579.

Kimura, N., et al., "An In Vivo Study of the Replication Origin in the Influenza Virus Complementary RNA", *The Journal of Biochemistry*, 113(1), (1993),88-92.

Kimura, N., et al., "Transcription of a Recombinant Influenza Virus RNA in Cells That Can Express the Influenza Virus RNA Polymerase and Nucleoprotein Genes", *Journal of General Virology*, 73,(1992),1321-1328.

Kobayashi, M., et al., "Reconstitution of Influenza Virus RNA Polymerase From Three Subunits Expressed Using Recombinant Baculovirus System", *Virus Research*, 22, (1992),235-245.

Konarska, M. M., et al., "Structure of RNAs Replicated by the DNA-Dependent T7 RNA Polymerase", *Cell*, 63(2), (1990),609-618.

Krystal, M., et al., "Expression of the Three Influenza Virus Polymerase Proteins in a Single Cell Allows Growth Complementation of Viral Mutants", *Proc. Natl. Acad. Sci. USA*, 83, (1986),2709-2713.

Kunkel, T. A., "Rapid and Efficient Site-Specific Mutagenesis Without Phenotypic Selection", *Proc. Natl. Acad. Sci. USA*, 82, (1985),488-492.

Lamb, et al., "Chapter 20—Paramyoxoviridae: The Viruses and Their Replication", *In: Fundamental Virology*, Fields, B. N., et al., Editors, Lippincott-Raven Publishers, (2nd Edition, 1996), 577-647.

Lawson, N. D., "Recombinant Vesicular Stomatitis Viruses From DNA", *Proc. Natl. Acad. Sci. USA*, 92(10), (1995),4477-4481

Levis, R., et al., "Deletion Mapping of Sindbis Virus DI RNAs Derived From cDNAs Defines the Sequences Essential for Replication and Packaging", *Cell*, 44, (1986),137-145.

Luytjes, W., et al., "Amplification, Expression, and Packaging of a Foriegn Gene by Influenza Virus", *Cell*, 59(6), (1989),1107-1113.

Mena, I., "Rescue of a Synthetic Choramphenicol Acetyltransferase RNA into influenza Virus-Like Particles obtained from recombinant plasmids", *Journal of Virology*, 70(8), (Aug. 1996),5016-5024.

Mena, I., et al., "Synthesis of Biologically Active Influenza Virus Core Proteins Using a Vaccinia Virus-T7 RNA Polymerase Expression System", *Journal of General Virology*, 75, (1994),2109-2114.

Moyer, S. A., et al., "Assembly and Transcription of Synthetic Vesicular Stomatitis Virus Nucleocapsids", *Journal of Virology*, 65(5), (1991),2170-2178.

Muster, T., "An Influenza A Virus Containing Influenza B Virus 5' and 3' Noncoding Regions on the Neuraminidase Gene is Attenuated in Mice", *Proceeding of the National Academy of Sciences USA*, 88, (Jun. 1991),5177-5181.

Naito, S., et al., "Function and Structure of RNA Polymerase From Vesicular Stomatitis Virus"; *The Journal of Biological Chemistry*, 251(14), (1976),4307-4314.

Nara, P. L., et al., "Simple, Rapid, Quantitative, Syncytium-Forming Microassay for the Detection of Human Immunodeficiency Virus Neutralizing Antibody", *Aids Research and Human Retroviruses*, 3(3), (1987),283-302.

Nemeroff, M. E., et al., "Influenza Virus NS1 Protein Interacts With the Cellular 30 kDa Subunit of CPSF and Inhibits 3' End Formation of Cellular Pre-mRNAs", *Molecular Cell*, 1(7), (1998),991-1000.

Neumann, G., "RNA Polymerase I-Mediated Expression of Influenza Viral RNA Molecules", *Virology*, 202(1), (Jul. 1994),477-479.

Palese, P., "Negative-Strand RNA Viruses: Genetic Engineering and Applications", *Proc. Natl. Acad. Sci. USA*,93(21), (1996),11354-11358.

Park, K. H., et al., "Rescue of a Foreign Gene by Sendai Virus", *Proc. Natl. Acad. Sci. USA*, 88, (1991),5537-5541.

Pattnaik, A. K., et al., "Cells That Express All Five Proteins of Vesicular Stomatitis Virus From Cloned cDNAs Support Replication, Assembly, and Budding of Defective Interfering Particles", *Proc. Natl. Acad. Sci. USA*, 88, (1991),1379-1383.

Peeters, B. P., et al., "Rescue of Newcastle Disease Virus From Cloned cDNA: Evidence That Cleavability of the Fusion Protein Is a Major Determinant for Virulence", *Journal of Virology*, 73(6), (1999),5001-5009.

Pekosz, A., et al., "Commentary—Reverse Genetics of Negative-Strand RNA Viruses: Closing the Circle", *Proc. Natl. Acad. Sci. USA*, 96, (1999),8804-8806.

Percy, N., et al., "Expression of a Foreign Protein by Influenza A Virus", *Journal of Virology*, 68(7), (1994),4486-4492.

Pleschka, S., "A Plasmid-Based Reverse Gentics System for Influenza A Virus", *Journal of Virology*, 70(6), (Jun. 1996),4188-4192.

Qiu, Y., et al., "The Influenza Virus NS1 Protein Binds to a Specific Region in Human U6 snRNA and Inhibits U6-U2 and U6-U4 snRNA Interactions During Splicing", *RNA*, 1, (1995),304-316.

Qiu, Y., et al., "The Influenza Virus NS1 Protein Is a Poly(A)-Binding Protein That Inhibits Nuclear Export of mRNAs Containing Poly(A)", *Journal of Virology*, 68(4), (1994),2425-2432.

Racaniello, V. R., et al., "Cloned Poliovirus Complimentary DNA Is Infectious in Mammalian Cells", *Science*, 214 (1981), 916-919.

Radecke, F., et al., "Rescue of Measles Viruses From Cloned DNA", *The EMBO Journal*, 14(23), (1995),5773-5784.

Radecke, F., et al., "Reverse Genetics Meets the Nonsegmented Negative-Strand RNA Viruses", *Reviews in Medical Virology*, 7, (1997),49-63.

Roberts, A., et al., "Minireview—Recovery of Negative-Strand RNA Viruses From Plasmid DNAs: A Positive Approach Revitalizes a Negative Field", *Virology*, 247(1), (1998),1-6.

Rose, J. K., "Positive Strands to the Rescue Again: A Segmented Negative-Strand RNA Virus Derived From Cloned cDNAs", *Proc. Natl. Acad. Sci. USA*, 94, (1996),14998-15000.

Schlesinger, S., "RNA Viruses as Vectors for the Expression of Heterologous Proteins", *Molecular Biotechnology*, 3(2), (1995),155-165.

Schnell, M. J., "Infectious Rabies Viruses From Cloned cDNA", *The EMBO Journal*, 13(18), (1994),4195-4203.

Seong, B. L., et al., "A New Method for Reconstituting Influenza Polymerase and RNA in Vitro: A Study of the Promoter Elements for cRNA and vRNA Synthesis in Vitro and Viral Rescue in Vivo", *Virology*, 186(1), (1992),247-260.

Sidhu, M. S., et al., "Rescue of Synthetic Measles Virus Minireplicons: Measles Genomic Termini Direct Efficient Expression and Propagation of a Reporter Gene", *Virology*, 208, (1995),800-807.

Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influenza A Virus Vaccine", *Journal of Virology*, 69(10), (1995),5969-5977.

Szewczyk, B., "Purification, Thioredoxin Renaturation, and Reconstituted Activity of the Three Subunits of the Influenza A Virus RNA Polymerase", *Proc. Natl. Acad. Sci. USA*, 85, (1988),7907-7911.

Taylor, J., et al., "Newcastle Disease Virus Fusion Protein Expressed in a Fowlpox Virus Recombinant Confers Protection in Chickens", *Journal of Virology*, 64(4), (1990),1441-1450.

Ward, C. D., et al., "Direct Measurement of the Poliovirus RNA Polymerase Error Frequency In Vitro", *Journal of Virology*, 62(2), (1988),558-562.

Whelan, S. P., et al., "Efficient Recovery of Infectious Vesicular Stomatitis Virus Entirely from cDNA Clones", *Proc. Natl. Acad. Sci. USA*, 92, (1995),8388-8392.

Yamanaka, K., et al., "In Vivo Analysis of the Promoter Structure of the Influenza Virus RNA Genome Using a Transfection System With an Engineered RNA", *Proc. Natl. Acad. Sci. USA*, 88, (1991),5369-5373.

Yu, Q., et al., "Functional cDNA Clones of the Human Respiratory Syncytial (RS) Virus N, P, and L Proteins Support Replication of RS Virus Genomic RNA Analogs and Define Minimal *trans*-Acting Requirements for RNA Replication", *Journal of Virology*, 69(4), (1995),2412-2419.

Yusoff, K., et al., "Nucleotide Sequence Analysis of the L Gene of Newcastle Disease Virus: Homologies With Sendai and Vesicular Stomatitis Viruses", *Nucleic Acids Research*, 15(10), (1987),3961-3976.

Zaghouani, H., et al., "Cells Expressing an H Chain g Gene Carrying a Viral T Cell Epitope are Lysed by Specific Cytolytic T Cells", *The Journal of Immunology*, 148(11), (1992),3604-3609

Zaghouani, H , et al., "Induction of Antibodies to the Envelope Protein of the Human Immunodeficiency Virus by Immunization With Monoclonal Anti-Idiotypes", *Proc. Natl. Acad. Sci. USA*, 88, (1991),5645-5649.

Zhang, H. , et al., "Expression of Functional Influenza Virus A Polymerase Proteins and Template From Cloned cDNAs in Recombinant Vaccinia Virus Infected Cells", *Biochemical and Biophysical Research Communications*, 200(1), (1994),95-101.

Zobel, A. , et al., "RNA Polymerase I Catalysed Transcription of Insert Viral cDNA", *Nucleic Acids Research*, 21(16), (1993),3607-3614.

Kawaoka,Y. , "Signal for Packaging of Influenza Virus Vectors", U.S. Appl. No. 22/509,249, filed Aug. 24, 2006.

"Australian Application Serial No. 2004249133, First Examiner's Report mailed May 5, 2008", ERTR,8.

"New Zealand Application Serial No. 543446, Examination Report mailed May 2, 2008", ERTR-1,2.

"Korean Application Serial No. 10-2005-7022564, Office Action mailed 8-06-08", FOAR-MISC,5.

"Eurasian Application Serial No. 200501890, Office Action mailed Mar. 23, 2007 (w/ English Translation)", 2 pgs.

"Eurasian Application Serial No. 200501890, Office Action mailed Dec. 17, 2007 (w/ English Translation)", 6 pgs.

"Eurasian Application Serial No. 200501890, Office Action mailed Sep. 4, 2008", (English Translation), 1 pg.

"Eurasian Application Serial No. 200501890, Response filed Mar. 26, 2008 to Office Action mailed Dec. 17, 2007", (w/ English Translation of Claims), 15 pgs.

"Eurasian Application Serial No. 200501890, Response filed Jun. 14, 2007 to Office Action mailed Mar. 23, 2007 (w/ English Translation of Claims)", 11 pgs.

"Eurasian Application Serial No. 200501890, Response filed Dec. 17, 2008 to Office Action", 8 pgs.

"Eurasian Application Serial No. 200501890, Response filed Dec. 17, 2008 to Office Action mailed Sep. 4, 2008", (w/ English Translation of Claims), 2 pgs.

"European Application Serial No. 04776133.3, Communication mailed Mar. 30, 2006", 3 pgs.

"European Application Serial No. 04776133.3, Response filed Jan. 25, 2007 to Communication mailed Mar. 30, 2006", 20 pgs.

"Indian Application Serial No. 2272/KOLNP/2005, First Examination Report mailed Mar. 17, 2008", 10 pgs.

"Indian Application Serial No. 2272/KOLNP/2005, Response filed Mar. 16, 2009 to Subsequent Examination Report mailed Mar. 6, 2009", 12 pgs.

"Indian Application Serial No. 2272/KOLNP/2005, Response filed Oct. 31, 2008 to First Examination Report mailed Mar. 17, 2008", 27 pgs.

"Indian Application Serial No. 2272/KOLNP/2005, Subsequent Examination Report mailed Mar. 6, 2009", 1 pg.

"International Application Serial No. PCT/US2004/016680, International Preliminary Report on Patentability mailed Dec. 15, 2005", 11 pgs.

"Israel Application Serial No. 171831, Notification of Defects on Nov. 10, 2008 (English Translation)", 10 pgs.

"Korean Application Serial No. 10-2005-7022564, Amendment and Response filed Mar. 25, 2008 to Notice of Preliminary Rejection dated Jul. 25, 2007 (w/ English Translation of Claims)", 35 pgs.

"Korean Application Serial No. 10-2005-7022564, Amendment and Response filed Dec. 29, 2008 to Office Action mailed Aug. 6, 2008", (w/ English Translation of Claims), 16 pgs.

"Korean Application Serial No. 10-2005-7022564, Notice of Preliminary Rejection dated Jul. 25, 2007", (w/ English Translation), 5 pgs.

"Mexico Application No. PA/a/2005/012712 , Official Action mailed on Mar. 5, 2009 (English Translation)", 2 pgs.

"New Zealand Application Serial No. 543446, Examination Report mailed Feb. 29, 2008", 2 pgs.

"New Zealand Application Serial No. 543446, Response mailed Mar. 20, 2008 to Examination Report mailed Feb. 29, 2008", 2 pgs.

"Singapore Application Serial No. 200507468-7, Examination Report mailed Mar. 19, 2008", 5 pgs.

"Singapore Application Serial No. 200507468-7, Invitation to Respond to Written Opinion mailed Jun. 12, 2007", 6 pgs.

"Singapore Application Serial No. 200507468-7, Response filed Nov. 7, 2007 to Invitation to Respond to Written Opinion mailed Jun. 12, 2007", 9 pgs.

"Ukraine Application Serial No. 200512619, Office Action Mailed on Feb. 27, 2009", 11 pgs.

Horimoto, T., et al., "Enhanced growth of seed viruses for H5N1 influenza vaccines", *Virology*, 366(1), (Sep. 15, 2007), 23-27.
Horimoto, T., et al., "The Development and Characterization of H5 Influenza Virus Vaccines Derived from a 2003 Human Isolate", *Vaccine*, 24(17), (2006), 3669-3676.
"Australian Application Serial No. 2004249133, Response filed Mar. 30, 2009 to First Examiner's Report mailed May 5, 2008", 30 pgs.
"Chinese Application Serial No. 200480021259.9, First Offiice Action issued on Aug. 24, 2007", (w/ English Translation), 9 pgs.
"Chinese Application Serial No. 200480021259.9, Response filed Mar. 7, 2008 to Offiice Action issued on Aug. 24, 2007", (w/ English Translation of Claims), 13 pgs.
"Korean Application Serial No. 10-2005-7022564, Response and Amendment filed Dec. 29, 2008 to Office Action mailed Aug. 6, 2008", (w/ English Translation of Claim Set), 16 pgs.
"Ukraine Application Serial No. 200512619, Response filed Apr. 8, 2009 to Office Action mailed on Feb. 27, 2009", (w/ English Translation of Amended Claims), 9 pgs.
"Application Serial No. 200480021259.9 Office Action Oct. 20, 2009", 7 pgs.
"Mexican Application Serial No. PA/a/2005/012712 ,Office Action Mailed Aug. 11, 2009", 5 pgs.
"Mexican Application No. PA/a/2005/012712 Office Action—mailed Jul. 21, 2009", 4.
200480021259.9, "Chinese Application No. 200480021259.9, Office Action mailed May 8, 2009", 3 pgs.
200501890, "Eurasian Application No. 200501890, Notice of Allowance mailed Jun. 23, 2009", 2 pgs.
200512619, "Ukrainese Application Serial No. 200512619 , Office Action mailed Jun. 17, 2009", 3 pgs.
Hoffmann, E., et al., "Eight-plasmid system for rapid generation of influenza virus vaccines.", *Vaccine*, 20(25-26), (Aug. 19, 2002), 3165-70.
Hoffmann, E., et al., "Rescue of influenza B virus from eight plasmids.", *Proc Natl Acad Sci U S A.*, 99(17), (Aug. 20, 2002), 11411-6
Neumann, G., et al., "Generation of influenza A virus from cloned cDNAs—historical perspective and outlook for the new millenium.", *Rev Med Virol.*, 12(1), (2002), 13-30.
Neumann, G., et al., "Generation of influenza A viruses entirely from cloned cDNAs", *Proc Natl Acad Sci U S A.*,96(16), (Aug. 3, 1999), 9345-50.
"Application No. 2006-533439; Office Action Response Filed Jul. 9, 2010", 25.
"Application Serial No. 2006-533439 Office Action mailed Mar. 9, 2010", 20 pgs.
"Chinese Application Serial No. 200480021259.9 , Office Action mailed May 6, 2010", 12 Pgs.
"European Application Serial No. 04776133.3, EP Office Action mailed Jan. 5, 2010", 4.
"European Application Serial No. 04776133.3, Response to Office Action filed Jul. 15, 2010", Response to Office Action, 9 pgs.
"Israel Application Serial No. 171831, Office Action mailed Feb. 21, 2010", 2.
"Maxican application serial No. PA/a/2005/012712 , office action mailed Jun. 9, 2010", 11.
"Maxican application serial No. PA/a/2005/012712 , office action mailed Dec. 11, 2009", 6 pgs.
"Mexican Patent Application No. PA/a/2005/012712, Office Action mailed May 12, 2010", 8.
"Ukraine Application Serial No. 200512619, Notice of Allowance mailed Jul. 5, 2010", 6.
"Canadian Application Serial No. 205962, Office Action received Jun. 22, 2011", 4 pgs.

"Chinese Application Serial No. 200480021259.9, Request for Reexamination filed Apr. 26, 2011", (w/ English Translation of Amended Claims), 23 pgs.

"Japanese Application Serial No. 2006-533439, Response filed Aug. 3, 2011 to Office Action mailed Feb. 15, 2011", (w/ English Translation of Amended Claims), 18 pgs.

Bancroft, C. T., et al., "Evidence for segment-nonspecific packaging of the influenza A virus genome", *J Virol.*, 76(14), (Jul. 2002), 7133-7139.

Wu, R., et al., "A live bivalent influenza vaccine based on a H9N2 virus strain", *Vaccine*, 28, (2010) 673-680.

"Canadian Application Serial No. 2,525,953, Office Action Response filed Dec. 22, 2011", 17 pgs.

"Application Serial No. 200480021259.9 Office Action Response Filed Aug. 20, 2010", 26 pgs.

"Chinese Application Serial No. 200480021259.9, Office Action mailed Jan. 11, 2011", 15 pgs.

"Japanese Application Serial No. 2006-533439,Office Action mailed Feb. 15, 2011", 13 pgs.

"Mexican Application Serial No. PA/a/2005/012712, Notice of Allowance mailed Feb. 16, 2011".

"Mexican Patent Application No. PA/a/2005/012712 , Office Action Response Filed Sep. 27, 2010", 13.

Hoffmann, E., et al., "Eight-plasmid system for rapid generation of influenza virus vaccines", Vaccine, 20(25-26), (Aug. 19, 2002), 3165-70.

Hoffmann, E., et al., "Rescue of influenza B virus from eight plasmids.", Proc Natl Acad Sci U S A., 99(17), (Aug. 20, 2002), 11411-6.

Neumann, G., et al., "Generation of influenza A virus from cloned cDNAs—historical perspective and outlook for the new millenium", Rev Med Virol., 12(1), (Jan.-Feb. 2002), 13-30.

Neumann, G., et al., "Plasmid-driven formation of influenza virus-like particles", J Virol., 74(1), (Jan. 2000), 547-51.

Schickli, J. H, et al., "Plasmid-only rescue of influenza A virus vaccine candidates.", Philos Trans R Soc Lond B Biol Sci., 356(1416), (Dec. 29, 2001), 1965-73.

Subbarao, K., et al., "Evaluation of a genetically modified reassortant H5N1 influenza A virus vaccine candidate generated by plasmid-based reverse genetics.", Virology, 305(1), (Jan. 5, 2003), 192-200.

"Brazilian Application Serial No. PI0410702-0, Reponse filed May 7, 2012 to Office Action mailed Mar. 13, 2012", (w/ English Translation of Claims). 11 pgs.

"Japanese Application Serial No. 2006-533439, Response filed May 21, 2012 to Office Action mailed Mar. 27, 2012", (w/ English Translation of Amended Claims), 19 pgs.

"Mexican Application Serial No. MX/a/2009/006341, Response filed Jun. 4, 2012", 12 pgs.

"Canadian Application Serial No. 2,525,953, Office Action mailed Jul. 31, 2012", 4 pgs.

"Chinese Application Serial No. 200480021259.9, Office Action mailed Jul. 3, 2012", (w/ English Translation), 10 pgs.

"Chinese Application Serial No. 200480021259.9, Response filed Oct. 16, 12 to Office Action mailed Jul. 3, 2012", (w/ English Translation of Claims), 13 pgs.

"Israeli Application Serial No. 171831, Office Action mailed Apr. 18, 2012", (English Translation), 2 pgs.

"Israeli Application Serial No. 171831, Response filed Nov. 6, 2012 to Office Action mailed Apr. 18, 2012", (w/ English Translation of Amended Claims), 54 pgs.

"Japanese Application Serial No. 2006-533439, Decision of Final Rejection mailed Aug. 14, 2012", (w/ English Translation), 5 pgs.

"Brazilian Application Serial No. PI0410702-0, Office Action mailed Mar. 13, 2012", 2 pgs.

"Japanese Application Serial No. 2006-533439, Office Action mailed Mar. 27, 2012", w/ English Translation, 8 pgs.

"Mexican Application Serial No. MX/a/2009/006341—Office Action", 2 pgs.

* cited by examiner

H5N1-PR8

$10^{10}$ EID$_{50}$/ml
HA titer: 1:3,200

Fig 4

A/PR/8/34 (H1N1)

$10^{10}$ EID$_{50}$/ml
HA titer: 1:8,000

HIGH TITER RECOMBINANT INFLUENZA VIRUSES FOR VACCINES AND GENE THERAPY

CROSS-REFERENCE TO RELATED APPLICATIONS

The present application claims the benefit under 35 U.S.C. §119(e) of the filing date of U.S. application Ser. No. 60/473,798, filed May 28, 2003, the disclosure of which is incorporated by reference herein.

STATEMENT OF GOVERNMENT RIGHTS

This invention was made with a grant from the Government of the United States of America (grant AI-47446 from the National Institute of Allergy and Infectious Diseases Public Health Service). The Government may have certain rights in the invention.

BACKGROUND OF THE INVENTION

Negative-sense RNA viruses are classified into seven families (*Rhabdoviridae, Paramyxoviridae, Filoviridae, Bornaviridae, Orthomyxoviridae, Bunyaviridae,* and *Arenaviridae*) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB 1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

In order to initiate viral replication of negative-stranded RNA viruses, vRNA(s) or cRNA(s) must be coexpressed with the polymerase complex and the nucleoprotein. Rabies virus was the first non-segmented negative-sense RNA virus which was generated entirely from cloned cDNA: Schnell et al. (1994) generated recombinant rabies virus by cotransfection of a cDNA construct encoding the full-length cRNA and protein expression constructs for the L, P, and N proteins, all under control of the T7 RNA polymerase promoter. Infection with recombinant vaccinia virus, which provided T7 RNA polymerase, resulted in the generation of infectious rabies virus. In this T7 polymerase system, the primary transcription of the full length cRNA under control of the T7 RNA polymerase resulted in a non-capped cRNA transcript. However, three guanidine nucleotides, which form the optimal initiation sequence for T7 RNA polymerase, were attached to the 5' end. In order to create an authentic 3' end of the cRNA transcript which is essential for a productive infective cycle, the hepatitis delta ribozyme (HDVRz) sequence was used for exact autocatalytic cleavage at the 3' end of the cRNA transcript.

Since the initial report by Schnell et al. (1994), reverse genetics systems using similar techniques led to the generation of many non-segmented negative strand RNA viruses (Conzelmann, 1996; Conzelmann, 1998; Conzelmann et al., 1996; Marriott et al., 1999; Munoz et al., 2000; Nagai, 1999; Neumann et al., 2002; Roberts et al., 1998; Rose, 1996). Refinements of the original rescue procedure included the expression of T7 RNA polymerase from stably transfected cell lines (Radecke et al., 1996) or from protein expression plasmids (Lawson et al., 1995), or heat shock procedures to increase rescue efficiencies (Parks et al., 1999). Based on the T7 polymerase system, Bridgen and Elliott (1996) created Bunyamwera virus (family Bunyaviridae) from cloned cDNAs and demonstrated the feasibility of artificially generating a segmented negative-sense RNA virus by the T7 polymerase system.

In 1999, a plasmid-based reverse genetics technique was generated based on the cellular RNA polymerase I for the generation of segmented influenza A virus entirely from cloned cDNAs (Fodor et al., 1999; Neumann and Kawaoka, 1999). RNA polymerase I, a nucleolar enzyme, synthesizes ribosomal RNA which, like influenza virus RNA, does not contain 5' cap or 3' polyA structures. The RNA polymerase I transcription of a construct containing an influenza viral cDNA, flanked by RNA polymerase I promoter and terminator sequences, resulted in influenza vRNA synthesis (Fodor et al., 1999; Neumann and Kawaoka, 1999; Neumann and Kawaoka, 2001; Pekosz et al., 1999). The system was highly efficient, producing more than $10^8$ infectious virus particles per ml of supernatant of plasmid-transfected cells 48 hours post-transfection.

What is needed is a method to prepare high titer orthomyxoviruses such as influenza A virus, entirely from cloned cDNAs.

SUMMARY OF THE INVENTION

The invention provides an isolated and/or purified nucleic acid molecule (polynucleotide) encoding at least one of the proteins of a high titer, e.g., titers greater than $10^9$/ml, e.g., greater than $10^{10}$/ml, influenza virus, or a portion thereof, or the complement of the nucleic acid molecule. In one embodiment, the isolated and/or purified nucleic acid molecule encodes HA, NA, PB1, PB2, PA, NP, M, or NS, or a portion thereof having substantially the same activity as a corresponding polypeptide encoded by one of SEQ ID NOs:1-8. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the isolated and/or purified nucleic acid molecule encodes a polypeptide which is substantially the same as, e.g., having at least 80%, e.g., 90%, 92%, 95%, 97% or 99%, contiguous amino acid sequence identity to, a polypeptide encoded by one of SEQ ID NOs:1-8. In one embodiment, the isolated and/or purified nucleic acid molecule comprises a nucleotide sequence which is substantially the same as, e.g., having at least 50%, e.g., 60%, 70%, 80% or 90% or more contiguous nucleic acid sequence identity to, one of SEQ ID NOs:1-8, or the complement thereof, and, in one embodiment, also encodes a polypeptide having at least 80%, e.g., 90%, 92%, 95%, 97% or 99%, contiguous amino acid sequence identity to a polypeptide encoded by one of SEQ ID NOs:1-8. In one embodiment, the isolated and/or purified nucleic acid molecule encodes a polypeptide with one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1-8. "Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. Preferred conservative amino acid substitution groups are: valine-leucine-isoleucine; phenylalanine-tyrosine; lysine-arginine; alanine-valine; glutamic-aspartic; and asparagine-glutamine.

In another embodiment, the isolated and/or purified nucleic acid molecule of the invention or the complement thereof, hybridizes to one of SEQ ID NOs:1-8, or the complement thereof, under low stringency, moderate stringency or stringent conditions. For example, the following conditions may be employed: 7% sodium dodecyl sulfate (SDS), 0.5 M $NaPO_4$, 1 mM EDTA at 50° C. with washing in 2×SSC, 0.1% SDS at 50° C. (low stringency), more desirably in 7% sodium dodecyl sulfate (SDS), 0.5 M $NaPO_4$, 1 mM EDTA at 50° C. with washing in 1×SSC, 0.1% SDS at 50° C. (moderate stringency), more desirably still in 7% sodium dodecyl sulfate (SDS), 0.5 M $NaPO_4$, 1 mM EDTA at 50° C. with washing in 0.5×SSC, 0.1% SDS at 50° C. (stringent), preferably in 7% sodium dodecyl sulfate (SDS), 0.5 M $NaPO_4$, 1 mM EDTA at 50° C. with washing in 0.1×SSC, 0.1% SDS at 50° C. (more stringent), more preferably in 7% sodium dodecyl sulfate (SDS), 0.5 M $NaPO_4$, 1 mM EDTA at 50° C. with washing in 0.1×SSC, 0.1% SDS at 65° C. (very stringent). In one embodiment, the nucleic acid molecule of the invention encodes a polypeptide which is substantially the same as, e.g., having at least 50%, e.g., 60%, 70%, 80% or 90% or more contiguous nucleic acid sequence identity to, one of SEQ ID NOs:1-8, and preferably has substantially the same activity as a corresponding full-length polypeptide encoded by one of SEQ ID NOs:1-8.

The nucleic acid molecule of the invention may be employed to express influenza proteins, to prepare chimeric genes, e.g., with other viral genes including other influenza virus genes, and/or to prepare recombinant virus. Thus, the invention also provides isolated polypeptides, recombinant virus, and host cells contacted with the nucleic acid molecules or recombinant virus of the invention.

The invention also provides at least one of the following isolated and/or purified vectors: a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, a vector comprising a promoter operably linked to an influenza virus NS cDNA linked to a transcription termination sequence, wherein at least one vector comprises sequences encoding HA, NA, PB1, PB2, PA, NP, M, NS, or a portion thereof, having substantially the same activity as a corresponding polypeptide encoded by one of SEQ ID NOs:1-8, e.g., a sequence encoding a polypeptide with at least 80% amino acid identity to a polypeptide encoded by one of SEQ ID NOs:1-8. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

The invention provides isolated and purified vectors or plasmids, which express or encode influenza virus proteins, or express or encode influenza vRNA, both native and recombinant vRNA. Preferably, the vectors comprise influenza cDNA, e.g., influenza A (e.g., any influenza A gene including any of the 15 HA or 9 NA subtypes), B or C DNA (see Chapters 45 and 46 of Fields *Virology* (Fields et al. (eds.), Lippincott-Raven Publ., Philadelphia, Pa. (1996), which are specifically incorporated by reference herein), although it is envisioned that the gene(s) of any organism may be employed in the vectors or methods of the invention. The cDNA may be in the sense or antisense orientation relative to the promoter. Thus, a vector of the invention may encode an influenza virus protein (sense) or vRNA (antisense). Any suitable promoter or transcription termination sequence may be employed to express a protein or peptide, e.g., a viral protein or peptide, a protein or peptide of a nonviral pathogen, or a therapeutic protein or peptide.

The invention provides a composition comprising a plurality of influenza virus vectors of the invention. In one embodiment of the invention, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence, wherein at least one vector comprises a promoter operably linked to a nucleic acid molecule of the invention linked to a transcription termination sequence; and b) at least two vectors selected from a vector encoding influenza virus PA, a vector encoding influenza virus PB1, a vector encoding influenza virus PB2, and a vector encoding influenza virus NP. Optionally, the vectors of b) include one or more vectors encoding NP, NS, M, e.g., M1 and M2, HA or NA. Preferably, the vectors encoding viral proteins further comprise a transcription termination sequence.

In another embodiment, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA and NB cDNA linked to a transcription termination sequence, a vector comprising a promoter operably linked to an influenza virus M cDNA linked to a transcription termination sequence, a vector comprising a operably linked to an influenza virus NS cDNA linked to a transcription termination sequence, and a vector comprising a promoter operably linked to an influenza virus BM2 cDNA operably linked to a transcription sequence, wherein at least one vector comprises a promoter operably linked to a nucleic acid molecule of the invention linked to a transcription termination sequence; and b) at least two vectors selected from a vector encoding influenza virus PA, a vector encoding influenza virus PB1, a vector encoding influenza virus PB2, and a vector encoding influenza virus NP. Optionally, the vectors of b) include one or more vectors encoding NP, NS, M, HA or NA. Preferably, the vectors encoding viral proteins further comprise a transcription termination sequence.

A composition of the invention may also comprise a gene or open reading frame of interest, e.g., a foreign gene encoding an immunogenic peptide or protein useful as a vaccine. Thus, another embodiment of the invention comprises a composition of the invention as described above in which one of the vectors is replaced with, or the composition further comprises, a vector comprising a promoter linked to 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof, linked to a transcription termination sequence. Preferably, the desired nucleic acid sequence such as a cDNA is in an antisense orientation. The introduction of such a composition to a host cell permissive for influenza virus replication results in recombinant virus comprising vRNA corresponding to sequences of the vector. The promoter in such a vector for vRNA production may be a RNA polymerase I promoter, a RNA polymerase II promoter, a RNA polymerase III promoter, a T7 promoter, and a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. In one embodiment, the vector comprising the desired nucleic acid sequence comprises a cDNA of interest. The cDNA of interest, whether in a vector for vRNA or protein production, may encode an immunogenic epitope, such as an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes.

A plurality of the vectors of the invention may be physically linked or each vector may be present on an individual plasmid or other, e.g., linear, nucleic acid delivery vehicle.

The promoter or transcription termination sequence in a vRNA or virus protein expression vector may be the same or different relative to the promoter or any other vector. Preferably, the vector or plasmid which expresses influenza vRNA comprises a promoter suitable for expression in at least one particular host cell, e.g., avian or mammalian host cells such as canine, feline, equine, bovine, ovine, or primate cells including human cells, or preferably, for expression in more than one host.

In one embodiment, one or more vectors for vRNA production comprise a promoter including, but not limited to, a RNA polymerase I promoter, e.g., a human RNA polymerase I promoter, a RNA polymerase II promoter, a RNA polymerase III promoter, a T7 promoter, or a T3 promoter. Preferred transcription termination sequences for the vRNA vectors include, but are not limited to, a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2 and preferably more, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

The invention also provides a method to prepare influenza virus. The method comprises contacting a cell with a plurality of the vectors of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or virus of the invention. In another embodiment, the invention includes contacting the cell with one or more vectors, either vRNA or protein production vectors, prior to other vectors, either vRNA or protein production vectors.

The method of the invention allows easy manipulation of influenza viruses, e.g., by the introduction of attenuating mutations into the viral genome. Further, because influenza viruses induce strong humoral and cellular immunity, the invention greatly enhances these viruses as vaccine vectors, particularly in view of the availability of natural variants of the virus, which may be employed sequentially, allowing repetitive use for gene therapy.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) is provided.

The invention also provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor-specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. Preferably, the mammal is a human.

BRIEF DESCRIPTION OF THE DRAWINGS

FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

FIG. 2. Schematic diagram of the generation of RNA polymerase I constructs. cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA. Influenza A virus sequences are shown in bold face letters. (SEQ ID NOs:29-40)

FIG. 3. Proposed reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.

FIG. 4. Titer of various influenza viruses.

DETAILED DESCRIPTION OF THE INVENTION

Definitions

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation is generally obtained by in vitro culture and propagation and is substantially free from other infectious agents.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity. Similarly, influenza C virus does not have a M2 protein with ion channel activity. However, the CM1 protein is likely to have this activity. The activity of an ion channel protein may be measured by methods well-known to the art, see, e.g., Holsinger et al. (1994) and WO 01/79273.

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating replicated virus of the invention using known methods, such as, but not limited to, formalin or fB-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines.

Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the reasserted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants HINI and H3N2 vaccine candidates in a manner analogous to that described above for the A/AA/6/60 ca donor virus. Similarly, other known and suitable attenuated donor strains can be reassorted with influenza virus of the invention to obtain attenuated vaccines suitable for use in the vaccination of mammals (Enami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Avery's Drug Treatment, 1987; Osol, 1980; Katzung, 1992. The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscamet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; Avery, 1987; and Katzung, 1992. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Katsung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 μg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children 3 years of age, and 7.5 μg per component for older children <3 years of age. The quantity of NA can also be standardized, however, this glycoprotein can be labile during the processor purification and storage (Kendal et al., 1980). Each 0.5-ml dose of vaccine preferably contains approximately 1-50 billion virus particles, and preferably 10 billion particles.

The invention will be further described by the following examples.

Example 1

Materials and Methods

Cells and Viruses.

293T human embryonic kidney cells and Madin-Darby canine kidney cells (MDCK) were maintained in Dulbecco's modified Eagle medium (DMEM) supplemented with 10% fetal calf serum and in modified Eagle's medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10-day-old eggs.

Construction of Plasmids.

Figure 2:
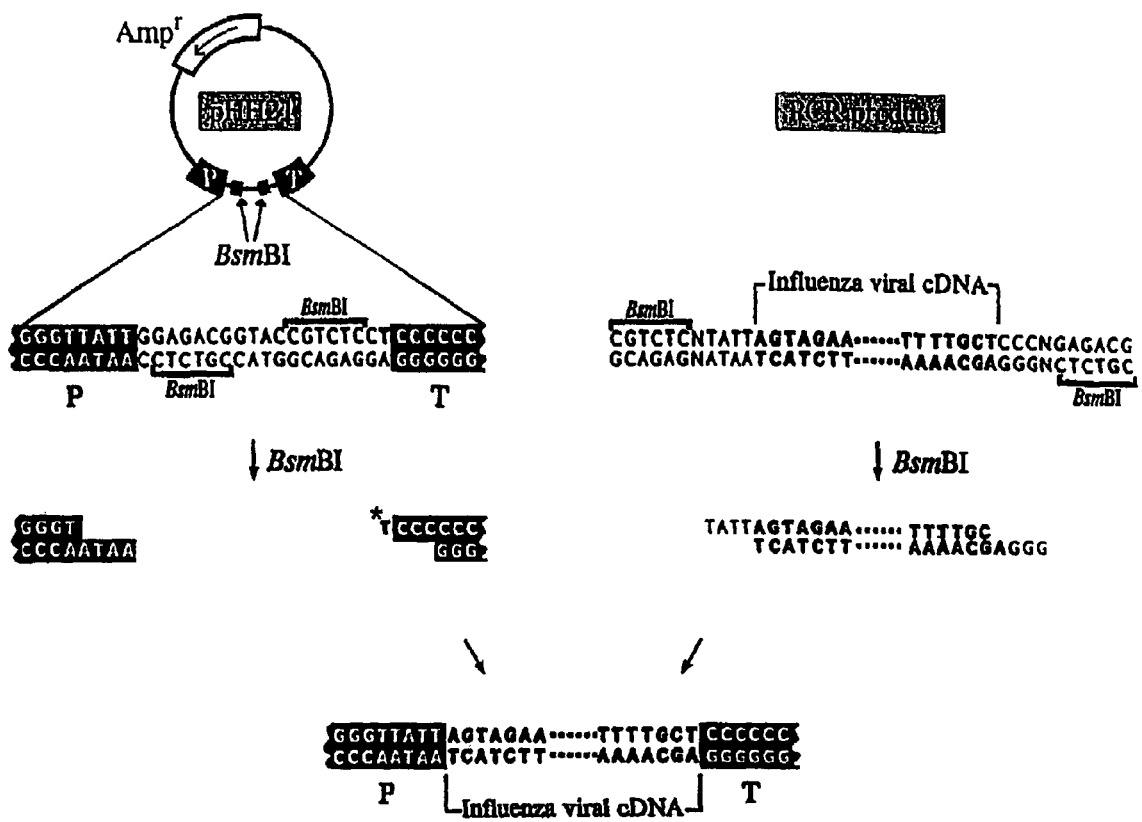

To generate RNA polymerase I constructs, cloned cDNAs derived from A/WSN/33 or A/PR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS1, respectively. The PB1 gene of influenza A/PR/8/34 virus was amplified by using pcDNA774 (PB1) (Perez et al., 1998) as a template. See FIG. 6 for the sequences of the primers. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of A/WSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN-NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774(PB1), pcDNA762(PB2), and pcDNA787(PA) were used to express the PB2, PB1, and PA proteins under control of the cytomegalovirus promoter (Perez et al., 1998).

Generation of Infectious Influenza Particles.

293T cells ($1 \times 10^6$) were transfected with a maximum of 17 plasmids in different amounts with use of Trans IT LT-1 (Panvera, Madison, Wis.) according to the manufacturer's instructions. Briefly, DNA and transfection reagent were mixed (2 µl Trans IT-LT-1 per µg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the Percentage of Plasmid-Transfected Cells Producing Viruses.

Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining Assay.

Nine hours after infection with influenza virus, cells were washed twice with phosphate-buffered saline (PBS) and fixed with 3.7% paraformaldehyde (in PBS) for 20 minutes at room temperature. Next, they were treated with 0.1% Triton X-100 and processed as described by Neumann et al. (1997).

Results

Generation of Infectious Virus by Plasmid-Driven Expression of Viral RNA Segments, Three Polymerase Subunits and NP Protein.

Figure 3:
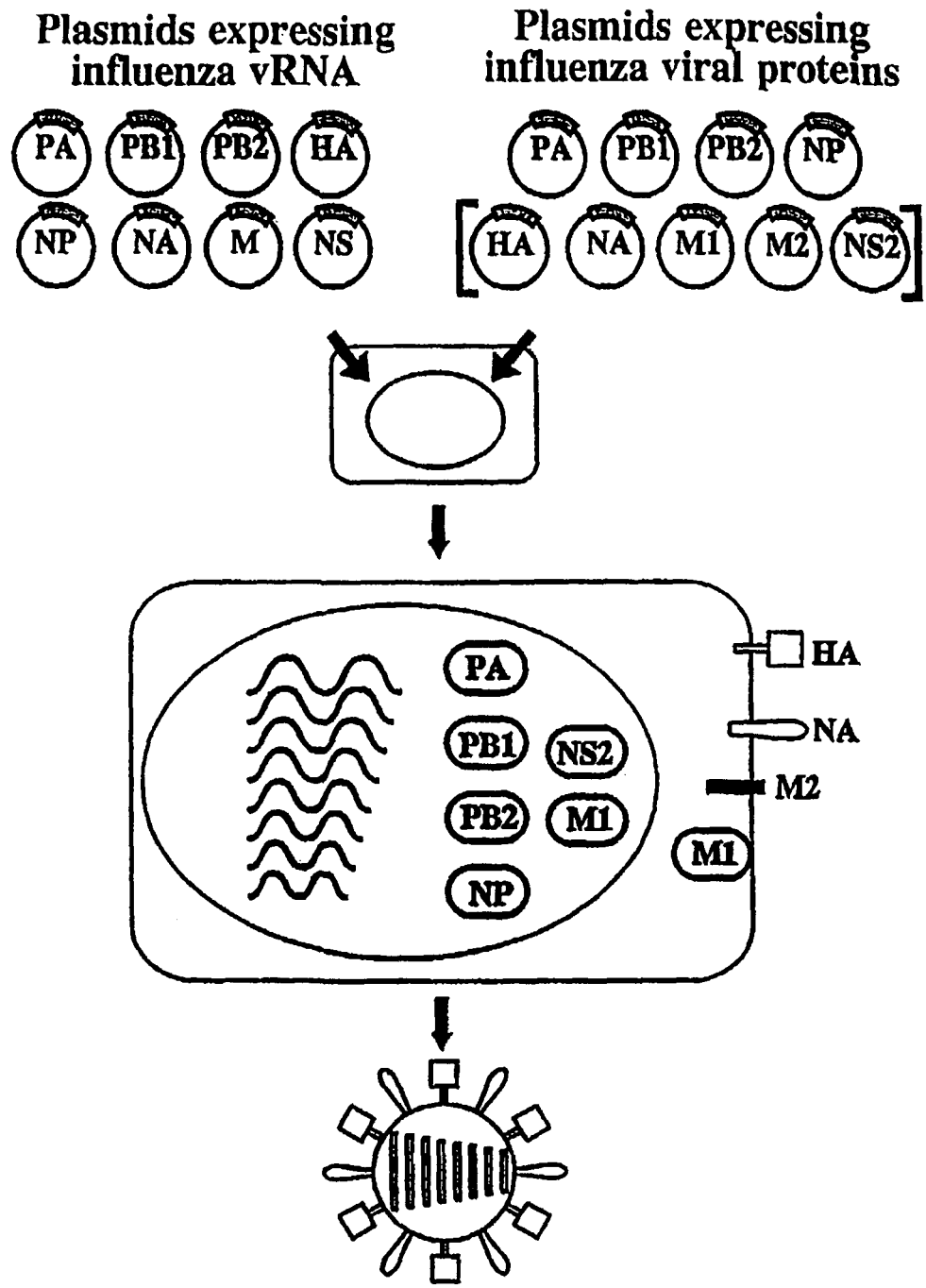

Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). $1 \times 10^6$ 293T cells were transfected with protein expression plasmids (1 µg of pcDNA762(PB2), 1 µg of pcDNA774(PB1), 0.1 µg of pcDNA787(PA), and 1 µg of pCAGGS-WSN-NP0/14) and 1 µg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after transfection of 293T cells, $7 \times 10^3$ pfu of virus per ml was found in the supernatant (Experiment 1, Table 1), demonstrating for the first time the capacity of reverse genetics to produce influenza A virus entirely from plasmids.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:† | | | | | | | | |
| PB1 | + | + | − | − | − | − | − | − |
| PR8-PB1 | − | − | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |

TABLE 1-continued

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| M | + | + | + | + | + | + | + | + |
| NS | + | + | + | + | + | + | + | + |
| Protein expression plasmids for: | | | | | | | | |
| PB1 | + | + | + | + | + |   | + | + |
| PB2 | + | + | + | + | + | + | − | + |
| PA | + | + | + | + | + | + | − | + |
| NP | + | + | + | + | + | + | + | − |
| HA | − | + | − | + | + | + | + | + |
| NA | − | + | − | + | + | + | + | + |
| M1 | − | + | − | + | + | + | + | + |
| M2 | − | + | − | + | + | + | + | + |
| NS2 | − | + | − | + | + | + | + | + |
| Virus titer (pfu/ml) | 7 × 10³ | 7 × 10³ | 1 × 10³ | 3 × 10⁴ | 0 | 0 | 0 | 0 |

*293T cells were transfected with the indicated plasmids. Twenty-four (Experiments 1 and 2) or forty-eight hours (Experiments 3-8) later, the virus titer in the supernatant was determined in MDCK cells.
†Unless otherwise indicated, plasmids were constructed with cDNAs representing the RNAs of A/WSN/33 virus.

Efficiency of influenza virus production with coexpression of all viral structural proteins. Although expression of the viral NP and polymerase proteins is sufficient for the plasmid-driven generation of influenza viruses, it was possible that the efficiency could be improved. In previous studies, the expression of all influenza virus structural proteins (PB2, PB11, PA, HA, NP, NA, M1, M2, and NS2) resulted in VLPs that contained an artificial vRNA encoding a reporter chloramphenicol-acetyltransferase gene (Mena et al., 1996). Thus, the availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 μg of pcDNA762 (PB2) and pcDNA774(PB1); 0.1 μg of pcDNA787(PA); 1 μg of pEWSN-HA, pCAGGS-WSN-NP0/14, and pCAGGS-WNA15; 2 μg of pCAGGS-WSN-M1-2/1; 0.3 μg of pCA-NS2; and 0.03 μg of pEP24c (for M2), together with 1 μg of each RNA polymerase I plasmid (Experiment 2, Table 1). A second set of cells was transfected with the same set of RNA polymerase I plasmids, with the exception of the PB13 gene, for which pPoII-PR/8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5-8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, >10³ pfu/ml, had increased to >10⁶ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in 103.3 cells was generating infectious virus particles.

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 2 |
| 6 | 0 | ND | ND |
| 12 | 0 | ND | 0 |
| 18 | 0 | ND | 0 |
| 24 | 0 | 2 × 10³ | 6 × 10³ |
| 30 | ND | 5 × 10⁴ | 9 × 10⁴ |
| 36 | 6 × 10² | >1 × 10⁵ | 7 × 10⁵ |
| 42 | ND | >1 × 10⁶ | 5 × 10⁶ |
| 48 | 8 × 10⁴ | >1 × 10⁶ | 1 × 10⁷ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Recovery of influenza virus containing the FLAG epitope in the NA protein. To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPoII-WSN-NA/FL79) that contained a cDNA encoding both the NA protein and a FLAG epitope at the bottom of the protein's head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus. Recovery of the PR8-WSN-FL79 virus was as efficient as that for the untagged wild-type virus (data not shown). These results indicate that the new reverse genetics system allows one to introduce mutations into the influenza A virus genome.

Generation of infectious influenza virus containing mutations in the PA gene. To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (*Bunyaviridae* family), but it contains only three segments of negative-sense RNA, and the efficiency of its production was low, $10^2$ pfu/$10^7$ cells. Although the virus yields differed among the experiments, consistently >$10^3$ pfu/106 cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991: Horimoto et al., 1994), NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. Having the technology to introduce any viable mutation into the influenza A virus genome enables investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel & Piedra, 1998), leaving room for further improvement. One possibility would be to modify a cold-adapted vaccine with the reverse genetics system described above. Alternatively, one could start from scratch by using reverse genetics to produce a "master" influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family *Orthomyxoviridae* comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., *Bunyaviridae, Arenaviridae*). The ability to manipulate the viral genome without technical limitations has profound implications for the study of viral life cycles and their regulation, the function of viral proteins and the molecular mechanisms of viral pathogenicity.

Example 2

To develop a reverse genetics system for influenza A/Puerto Rico/8/34, viral RNA was extracted from the allantoic fluid of A/Puerto Rico/8/34 (H1N1), Madison high grower variant (PR8HG), using RNeasy Mini kit (Qiagen) according to the manufacturer's protocol. cDNA was synthesized using MMLV-RTase (Promega) and Uni 12 primer. The cDNAs were amplified overnight by PCR using the following:

Primer sets

PB1: Ba PB1-1 and PB1-1735R (front fragment) and PB1-903 and Ba-PB1-2341R (rear fragment)

```
Ba-PB1-1
CACACACGGTCTCCGGGAGCGAAAGCAGGCA       (SEQ ID NO: 9)

173PB1-1735R
GGGTTTGTATTTGTGTGTCACC                (SEQ ID NO: 10)

233PB1-903
CCAGGACACTGAAATTTCTTTCAC              (SEQ ID NO: 11)

Ba-PB1-2341R
CACACAGGTCTCCTATTAGTAGAAACAAGGCATTT  (SEQ ID NO: 12)
```

PB2: Ba PB2-1 and B2 1260R (front fragment) and WSN PB2 seq-2 and Ba-PB2-2341R (rear fragment)

```
Ba-PB2-1
CACACAGGTCTCCGGGAGCGAAAGCAGGTC        (SEQ ID NO: 13)

B2 1260R
CACACACGTCTCCATCATACAATCCTCTTG        (SEQ ID NO: 14)

WSN PB2 seq-2
CTCCTCTGATGGTGGCATAC                  (SEQ ID NO: 15)

Ba-PB2-2341R
CACACAGGTCTCCTATTAGTAGAAACAAGGTCGTTT (SEQ ID NO: 16)

PA:
Bm-PA-1
CACACACGTCTCCGGGAGCGAAAGCAGGTAC       (SEQ ID NO: 17)

Bm-PA-2233R
CACACACGTCTCCTATTAGTAGAAACAAGGTACTT  (SEQ ID NO: 18)

HA:
Bm-HA-1:
CACACACGTCTCCGGGAGCAAAAGCAGGGG        (SEQ ID NO: 19)

Bm-NS-890R:
CACACACGTCTCCTATTAGTAGAAACAAGGGTGTTT (SEQ ID NO: 20)
T

NP:
Bm-NP-1
CACACACGTCTCCGGGAGCAAAAGCAGGGTA       (SEQ ID NO: 21)

Bm-NP-1565R
CACACACGTCTCCTATTAGTAGAAACAAGGGTATTT (SEQ ID NO: 22)
TT

NA:
Ba-NA-1:
CACACAGGTCTCCGGGAGCAAAAGCAGGAGT       (SEQ ID NO: 23)

Ba-NA-1413R:
CACACAGGTCTGGTATTAGTAGAAACAAGGAGTTTT (SEQ ID NO: 24)
TT

M:
Bm-M-1
CACACACGTCTCCGGGAGCAAAAGCAGGTAG       (SEQ ID NO: 25)

Bm-M-1027R
CACACACGTCTCCTATTAGTAGAAACAAGGTAGTTT (SEQ ID NO: 26)
TT
```

-continued

```
NS:
Bm-NS-1
CACACACGTCTCCGGGAGCAAAAGCAGGGTG       (SEQ ID NO: 27)

Bm-NS-890R
CACACACGTCTCCTATTAGTAGAAACAAGGGTGTTT (SEQ ID NO: 28)
T
```

DNA Polymerase: pfu Native DNA Polymerase (Stratagene)

The PCR products were separated by gel electrophoresis and extracted from the agarose gel using a gel extraction kit (Qiagen). The extracted genes were ligated into pT7Blue blunt vector (Novagen) using a Takara ligation kit ver. II (Takara). After 5 hours, the ligated genes were transformed into JM109 (PB2, M, and NS genes) or DHSalpha (PA, PB1, and NP). Six colonies for each gene were cultured in TB for 8 hours. The plasmids were extracted from the bacteria culture, and four clones per gene were sequenced.

The PA, NP, M, and NS genes in pT7Blue were excised by Bsm BI enzyme (New England Biolabs). The PB1 gene was excised by Bsa I (New England Biolabs). The excised genes were ligated overnight with pPolIR vector which contains the human RNA polymerase I promoter and the mouse RNA polymerase I terminator which had been digested with Bsm BI. The front fragment of the PB2 gene in pT7Blue was excised by Bsr GI (New England Biolabs) and Bam HI (Roche), and the rear fragment was excised by Bsr GI (New England Biolabs) and Spe I (Roche). The excised fragments were mixed and digested by Bsa I. After 6 hours, the digested genes were purified using a PCR purification kit (Qiagen) and ligated overnight between the Bsm BI sites of the pPolIR vector.

The ligated PB1, PA, NP, M, and NS-pPolIR genes were used to transform JM109 (M and NS genes) or DH5alpha (PB1, PA and NP genes) overnight. The colonies of transformed bacteria were cultured in LB overnight. The ligated PB2-pPolIR was used to transform JM109 overnight.

The plasmids were extracted from the bacterial cultures and gene inserts were confirmed by enzyme digestion. The colonies of bacteria transformed by PB2-PolIR were cultured in LB for 8 hours. The plasmids were then extracted and the gene insertion was confirmed by enzyme digestion. All pPolI constructs were sequenced to ensure that they did not contain unwanted mutations.

The pPolIR constructs for PR8HG were transfected into 293T human embryonic kidney cells with A/WSN/33(WSN)-HA and NA, A/Hong Kong/483/97(HK)-HAavir and NA, or A/Kawasaki/01(Kawasaki)-HA and NA PolI constructs and four protein-expression constructs for the polymerase proteins and NP of A/WSN/33. The supernatants from transfected 293T cells were serially diluted (undiluted to $10^{-7}$) and infected into the allantoic cavities of 9-day-old embryonated chicken eggs. The allantoic fluids of the infected eggs were harvested and their virus titers tested by HA assay (Table 3).

TABLE 3

| Virus possessing PR8 genes together with the following HA and NA genes | HA titer (HAU/ml) of allantoic fluid from eggs inoculated with 293T supernatants diluted at: | | | | | | | |
|---|---|---|---|---|---|---|---|---|
| | undiluted | $10^{-1}$ | $10^{-2}$ | $10^{-3}$ | $10^{-4}$ | $10^{-5}$ | $10^{-6}$ | $10^{-7}$ |
| WSN-HA NA | <1 | <1 | 200 | <1 | <1 | <1 | <1 | <1 |
| HK-HAavir NA | 100 | <1 | <1 | <1 | <1 | <1 | <1 | <1 |
| Kawasaki-HA NA | <1 | <1 | <1 | <1 | <1 | <1 | <1 | <1 |

HA-positive samples (virus with WSN-HA NA at $10^{-2}$ and virus with HK-HAavir NA at undiluted) were diluted serially from $10^{-2}$ to $10^{-8}$ and 100 ul of each dilution was infected into embryonated chicken eggs. The allantoic fluids of the infected eggs were harvested and their virus titers tested by HA assay (Table 4). The 50% egg infectious dose ($EID_{50}$) of A/Puerto Rico/8/34 (H1N1) prepared from plasmids was $10^{10.33}$/ml, and the HA titer was 1:3200.

A recombinant virus having the HA and NA genes from A/Hong Kong/213/2003 (H5N1) and the remainder of the type A influenza virus genes from PR8HG was prepared. The titer of the recombinant virus was $10^{10.67}$ $EID_{50}$/ml, and the HA titer was 1:1600

TABLE 4

| Virus possessing PR8 genes together with the following HA and NA genes | HA titer (HAU/ml) in each dilition | | | | | | |
|---|---|---|---|---|---|---|---|
| | $10^{-2}$ | $10^{-3}$ | $10^{-4}$ | $10^{-5}$ | $10^{-6}$ | $10^{-7}$ | $10^{-8}$ |
| WSN-HA NA | 160 | 40 | 40 | 320 | 40 | 640 | <1 |
| HK-HAavir NA | 400 | 800 | 400 | 400 | 400 | 800 | <1 |

Sequences of PR8 genes:

```
PA
AGCGAAAGCA GGTACTGATC CAAAATGGAA GATTTTGTGC GACAATGCTT  (SEQ ID NO: 1)

CAATCCGATG ATTGTCGAGC TTGCGGAAAA AACAATGAAA GAGTATGGGG

AGGACCTGAA AATCGAAACA AACAAATTTG CAGCAATATG CACTCACTTG

GAAGTATGCT TCATGTATTC AGATTTTCAC TTCATCAATG AGCAAGGCGA

GTCAATAATC GTAGAACTTG GTGATCCAAA TGCACTTTTG AAGCACAGAT

TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT

GTATGATTAC AAGGAGAATA GATTCATCGA AATTGGAGTA ACAAGGAGAG

AAGTTCACAT ATACTATCTG GAAAAGGCCA ATAAAATTAA ATCTGAGAAA

ACACACATCC ACATTTTCTC GTTCACTGGG GAAGAAATGG CCACAAAGGC

AGACTACACT CTCGATGAAG AAAGCAGGGC TAGGATCAAA ACCAGACTAT

TCACCATAAG ACAAGAAATG GCCAGCAGAG GCCTCTGGGA TTCCTTTCGT

CAGTCCGAGA GAGGAGAAGA GACAATTGAA GAAAGGTTTG AAATCACAGG

AACAATGCGC AAGCTTGCCG ACCAAAGTCT CCCGCCGAAC TTCTCCAGCC

TTGAAAATTT TAGAGCCTAT GTGGATGGAT TCGAACCGAA CGGCTACATT

GAGGGCAAGC TGTCTCAAAT GTCCAAAGAA GTAAATGCTA GAATTGAACC

TTTTTTGAAA ACAACACCAC GACCACTTAG ACTTCCGAAT GGGCCTCCCT

GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA

ATGCATGAGA ACATTCTTTG GATGGAAGGA ACCCAATGTT GTTAAACCAC

ACGAAAAGGG AATAAATCCA AATTATCTTC TGTCATGGAA GCAAGTACTG

GCAGAACTGC AGGACATTGA GAATGAGGAG AAAATTCCAA AGACTAAAAA

TATGAAGAAA ACAAGTCAGC TAAAGTGGGC ACTTGGTGAG AACATGGCAC

CAGAAAAGGT AGACTTTGAC GACTGTAAAG ATGTAGGTGA TTTGAAGCAA

TATGATAGTG ATGAACCAGA ATTGAGGTCG CTTGCAAGTT GGATTCAGAA
```

-continued

```
TGAGTTTAAC AAGGCATGCG AACTGACAGA TTCAAGCTGG ATAGAGCTCG

ATGAGATTGG AGAAGATGTG GCTCCAATTG AACACATTGC AAGCATGAGA

AGGAATTATT TCACATCAGA GGTGTCTCAC TGCAGAGCCA CAGAATACAT

AATGAAGGGA GTGTACATCA ATACTGCCTT GCTTAATGCA TCTTGTGCAG

CAATGGATGA TTTCCAATTA ATTCCAATGA TAAGCAAGTG TAGAACTAAG

GAGGGAAGGC GAAAGACCAA CTTGTATGGT TTCATCATAA AAGGAAGATC

CCACTTAAGG AATGACACCG ACGTGGTAAA CTTTGTGAGC ATGGAGTTTT

CTCTCACTGA CCCAAGACTT GAACCACATA AATGGGAGAA GTACTGTGTT

CTTGAGATAG GAGATATGCT TATAAGAAGT GCCATAGGCC AGGTTTCAAG

GCCCATGTTC TTGTATGTGA GAACAAATGG AACCTCAAAA ATTAAAATGA

AATGGGGAAT GGAGATGAGG CGTTGCCTCC TCCAGTCACT TCAACAAATT

GAGAGTATGA TTGAAGCTGA GTCCTCTGTC AAAGAGAAAG ACATGACCAA

AGAGTTCTTT GAGAACAAAT CAGAAACATG GCCCATTGGA GAGTCCCCCA

AAGGAGTGGA GGAAAGTTCC ATTGGGAAGG TCTGCAGGAC TTTATTAGCA

AAGTCGGTAT TCAACAGCTT GTATGCATCT CCACAACTAG AAGGATTTTC

AGCTGAATCA AGAAAACTGC TTCTTATCGT TCAGGCTCTT AGGGACAACC

TGGAACCTGG GACCTTTGAT CTTGGGGGGC TATATGAAGC AATTGAGGAG

TGCCTGATTA ATGATCCCTG GGTTTTGCTT AATGCTTCTT GGTTCAACTC

CTTCCTTACA CATGCATTGA GTTAGTTGTG GCAGTGCTAC TATTTGCTAT

CCATACTGTC CAAAAAGTA CCTTGTTTCT ACT
```

PB1

```
AGCGAAAGCA GGCAAACCAT TTGAATGGAT GTCAATCCGA       (SEQ ID NO: 2)

CCTTACTTTT CTTAAAAGTG CCAGCACAAA ATGCTATAAG CACAACTTTC

CCTTATACTG GAGACCCTCC TTACAGCCAT GGGACAGGAA CAGGATACAC

CATGGATACT GTCAACAGGA CACATCAGTA CTCAGAAAAG GGAAGATGGA

CAACAAACAC CGAAACTGGA GCACCGCAAC TCAACCCGAT TGATGGGCCA

CTGCCAGAAG ACAATGAACC AAGTGGTTAT GCCCAAACAG ATTGTGTATT

GGAGGCGATG GCTTTCCTTG AGGAATCCCA TCCTGGTATT TTTGAAAACT

CGTGTATTGA ACGATGGAG GTTGTTCAGC AAACACGAGT AGACAAGCTG

ACACAAGGCC GACAGACCTA TGACTGGACT CTAAATAGAA ACCAACCTGC

TGCAACAGCA TTGGCCAACA CAATAGAAGT GTTCAGATCA AATGGCCTCA

CGGCCAATGA GTCTGGAAGG CTCATAGACT TCCTTAAGGA TGTAATGGAG

TCAATGAACA AGAAGAAAT GGGGATCACA ACTCATTTTC AGAGAAAGAG

ACGGGTGAGA GACAATATGA CTAAGAAAAT GATAACACAG AGAACAATGG

GTAAAAGAA GCAGAGATTG AACAAAAGGA GTTATCTAAT TAGAGCATTG

ACCCTGAACA CAATGACCAA AGATGCTGAG AGAGGGAAGC TAAAACGGAG

AGCAATTGCA ACCCCAGGGA TGCAAATAAG GGGGTTTGTA TACTTTGTTG

AGACACTGGC AAGGAGTATA TGTGAGAAAC TTGAACAATC AGGGTTGCCA

GTTGGAGGCA ATGAGAAGAA AGCAAAGTTG GCAAATGTTG TAAGGAAGAT

GATGACCAAT TCTCAGGACA CCGAACTTTC TTTCACCATC ACTGGAGATA

ACACCAAATG GAACGAAAAT CAGAATCCTC GGATGTTTTT GGCCATGATC
```

-continued

```
ACATATATGA CCAGAAATCA GCCCGAATGG TTCAGAAATG TTCTAAGTAT
TGCTCCAATA ATGTTCTCAA ACAAAATGGC GAGACTGGGA AAAGGGTATA
TGTTTGAGAG CAAGAGTATG AAACTTAGAA CTCAAATACC TGCAGAAATG
CTAGCAAGCA TCGATTTGAA ATATTTCAAT GATTCAACAA GAAGAAGAT
TGAAAAAATC CGACCGCTCT AATAGAGGG GACTGCATCA TTGAGCCCTG
GAATGATGAT GGGCATGTTC AATATGTTAA GCACTGTATT AGGCGTCTCC
ATCCTGAATC TTGGACAAAA GAGATACACC AAGACTACTT ACTGGTGGGA
TGGTCTTCAA TCCTCTGACG ATTTTGCTCT GATTGTGAAT GCACCCAATC
ATGAAGGGAT TCAAGCCGGA GTCGACAGGT TTTATCGAAC CTGTAAGCTA
CTTGGAATCA ATATGAGCAA GAAAAGTCT TACATAAACA GAACAGGTAC
ATTTGAATTC ACAAGTTTTT TCTATCGTTA TGGGTTTGTT GCCAATTTCA
GCATGGAGCT TCCCAGTTTT GGGGTGTCTG GATCAACGA GTCAGCGGAC
ATGAGTATTG GAGTTACTGT CATCAAAAAC AATATGATAA ACAATGATCT
TGGTCCAGCA ACAGCTCAAA TGGCCCTTCA GTTGTTCATC AAAGATTACA
GGTACACGTA CCGATGCCAT ATAGGTGACA CACAAATACA ACCCGAAGA
TCATTTGAAA TAAAGAAACT GTGGGAGCAA ACCCGTTCCA AAGCTGGACT
GCTGGTCTCC GACGGAGGCC CAAATTTATA CAACATTAGA ATCTCCACA
TTCCTGAAGT CTGCCTAAAA TGGGAATTGA TGGATGAGGA TTACCAGGGG
CGTTTATGCA ACCCACTGAA CCCATTTGTC AGCCATAAAG AAATTGAATC
AATGAACAAT GCAGTGATGA TGCCAGCACA TGGTCCAGCC AAAAACATGG
AGTATGATGC TGTTGCAACA ACACACTCCT GGATCCCCAA AGAAATCGA
TCCATCTTGA ATACAAGTCA AGAGGAGTA CTTGAGGATG AACAAATGTA
CCAAAGGTGC TGCAATTTAT TTGAAAAATT CTTCCCCAGC AGTTCATACA
GAAGACCAGT CGGGATATCC AGTATGGTGG AGGCTATGGT TTCCAGAGCC
CGAATTGATG CACGGATTGA TTTCGAATCT GGAAGGATAA AGAAAGAAGA
GTTCACTGAG ATCATGAAGA TCTGTTCCAC CATTGAAGAG CTCAGACGGC
AAAAATAGTG AATTTAGCTT GTCCTTCATG AAAAAATGCC TTGTTTCTAC
T
PB2
AGCGAAAGCA GGTCAATTAT ATTCAATATG GAAAGAATAA AAGAACTACG (SEQ ID NO: 3)
AAATCTAATG TCGCAGTCTC GCACCCGCGA GATACTCACA AAACCACCG
TGGACCATAT GGCCATAATC AAGAAGTACA CATCAGGAAG ACAGGAGAAG
AACCCAGCAC TTAGGATGAA ATGGATGATG GCAATGAAAT ATCCAATTAC
AGCAGACAAG AGGATAACGG AAATGATTCC TGAGAGAAAT GAGCAAGGAC
AAACTTTATG GAGTAAAATG AATGATGCCG GATCAGACCG AGTGATGGTA
TCACCTCTGG CTGTGACATG GTGGAATAGG AATGGACCAA TAACAAATAC
AGTTCATTAT CCAAAAATCT ACAAAACTTA TTTTGAAAGA GTCGAAAGGC
TAAAGCATGG AACCTTTGGC CCTGTCCATT TTAGAAACCA AGTCAAAATA
CGTCGGAGAG TTGACATAAA TCCTGGTCAT GCAGATCTCA GTGCCAAGGA
GGCACAGGAT GTAATCATGG AAGTTGTTTT CCCTAACGAA GTGGGAGCCA
GGATACTAAC ATCGGAATCG CAACTAACGA TAACCAAAGA GAAGAAAGAA
```

-continued

```
GAACTCCAGG ATTGCAAAAT TTCTCCTTTG ATGGTTGCAT ACATGTTGGA

GAGAGAACTG GTCCGCAAAA CGAGATTCCT CCCAGTGGCT GGTGGAACAA

GCAGTGTGTA CATTGAAGTG TTGCATTTGA CTCAAGGAAC ATGCTGGGAA

CAGATGTATA CTCCAGGAGG GGAAGTGAGG AATGATGATG TTGATCAAAG

CTTGATTATT GCTGCTAGGA ACATAGTGAG AAGAGCTGCA GTATCAGCAG

ATCCACTAGC ATCTTTATTG GAGATGTGCC ACAGGACACA GATTGGTGGA

ATTAGGATGG TAGACATCCT TAGGCAGAAC CCAACAGAAG AGCAAGCCGT

GGATATATGC AAGGCTGCAA TGGGACTGAG AATTAGCTCA TCCTTCAGTT

TTGGTGGATT CACATTTAAG AGAACAAGCG GATCATCAGT CAAGAGAGAG

GAAGAGGTGC TTACGGGCAA TCTTCAAACA TTGAAGATAA GAGTGCATGA

GGGATATGAA GAGTTCACAA TGGTTGGGAG AAGAGCAACA GCCATACTCA

GAAAAGCAAC CAGGAGATTG ATTCAGCTGA TAGTGAGTGG GAGAGACGAA

CAGTCGATTG CCGAAGCAAT AATTGTGGCC ATGGTATTTT CACAAGAGGA

TTGTATGATA AAAGCAGTCA GAGGTGATCT GAATTTCGTC AATAGGGCGA

ATCAACGATT GAATCCTATG CATCAACTTT TAAGACATTT TCAGAAGGAT

GCGAAAGTGC TTTTTCAAAA TTGGGGAGTT GAACCTATCG ACAATGTGAT

GGGAATGATT GGGATATTGC CGACATGAC  TCCAAGCATC GAGATGTCAA

TGAGAGGAGT GAGAATCAGC AAAATGGGTG TAGATGAGTA CTCCAGCACG

GAGAGGGTAG TGGTGAGCAT TGACCGTTTT TTGAGAATCC GGGACCAACG

AGGAAATGTA CTACTGTCTC CCGAGGAGGT CAGTGAAACA CAGGGAACAG

AGAAACTGAC AATAACTTAC TCATCGTCAA TGATGTGGGA GATTAATGGT

CCTGAATCAG TGTTGGTCAA TACCTATCAA TGGATCATCA GAAACTGGGA

AACTGTTAAA ATTCAGTGGT CCCAGAACCC TACAATGCTA TACAATAAAA

TGGAATTTGA ACCATTTCAG TCTTTAGTAC CTAAGGCCAT TAGAGGCCAA

TACAGTGGGT TTGTAAGAAC TCTGTTCCAA CAAATGAGGG ATGTGCTTGG

GACATTTGAT ACCGCACAGA TAATAAAACT TCTTCCCTTC GCAGCCGCTC

CACCAAAGCA AAGTAGAATG CAGTTCTCCT CATTTACTGT GAATGTGAGG

GGATCAGGAA TGAGAATACT TGTAAGGGGC AATTCTCCTG TATTCAACTA

TAACAAGGCC ACGAAGAGAC TCACAGTTCT CGGAAAGGAT GCTGGCACTT

TAACTGAAGA CCCAGATGAA GGCACAGCTG GAGTGGAGTC CGCTGTTCTG

AGGGGATTCC TCATTCTGGG CAAAGAAGAC AAGAGATATG GGCCAGCACT

AAGCATCAAT GAACTGAGCA ACCTTGCGAA AGGAGAGAAG GCTAATGTGC

TAATTGGGCA AGGAGACGTG GTGTTGGTAA TGAAACGGAA ACGGGACTCT

AGCATACTTA CTGACAGCCA GACAGCGACC AAAAGAATTC GGATGGCCAT

CAATTAGTGT CGAATAGTTT AAAAACGACC TTGTTTCTAC T

NP

AGCAAAAGCA GGGTAGATAA TCACTCACTG AGTGACATCA           (SEQ ID NO: 4)

AAATCATGGC GTCTCAAGGC ACCAAACGAT CTTACGAACA GATGGAGACT

GATGGAGAAC GCCAGAATGC CACTGAAATC AGAGCATCCG TCGGAAAAAT

GATTGGTGGA ATTGGACGAT TCTACATCCA AATGTGCACC GAACTCAAAC

TCAGTGATTA TGAGGGACGG TTGATCCAAA ACAGCTTAAC AATAGAGAGA
```

```
ATGGTGCTCT CTGCTTTTGA CGAAAGGAGA AATAAATACC TTGAAGAACA
TCCCAGTGCG GGGAAAGATC CTAAGAAAAC TGGAGGACCT ATATACAGGA
GAGTAAACGG AAAGTGGATG AGAGAACTCA TCCTTTATGA CAAAGAAGAA
ATAAGGCGAA TCTGGCGCCA AGCTAATAAT GGTGACGATG CAACGGCTGG
TCTGACTCAC ATGATGATCT GGCATTCCAA TTTGAATGAT GCAACTTATC
AGAGGACAAG AGCTCTTGTT CGCACCGGAA TGGATCCCAG GATGTGCTCT
CTGATGCAAG GTTCAACTCT CCCTAGGAGG TCTGGAGCCG CAGGTGCTGC
AGTCAAAGGA GTTGGAACAA TGGTGATGGA ATTGGTCAGA ATGATCAAAC
GTGGGATCAA TGATCGGAAC TTCTGGAGGG GTGAGAATGG ACGAAAAACA
AGAATTGCTT ATGAAAGAAT GTGCAACATT CTCAAAGGGA AATTTCAAAC
TGCTGCACAA AAAGCAATGA TGGATCAAGT GAGAGAGAGC CGGAACCCAG
GGAATGCTGA GTTCGAAGAT CTCACTTTTC TAGCACGGTC TGCACTCATA
TTGAGAGGGT CGGTTGCTCA CAAGTCCTGC CTGCCTGCCT GTGTGTATGG
ACCTGCCGTA GCCAGTGGGT ACGACTTTGA AGGGAGGGA TACTCTCTAG
TCGGAATAGA CCCTTTCAGA CTGCTTCAAA ACAGCCAAGT GTACAGCCTA
ATCAGACCAA ATGAGAATCC AGCACACAAG AGTCAACTGG TGTGGATGGC
ATGCCATTCT GCCGCATTTG AAGATCTAAG AGTATTAAGC TTCATCAAAG
GGACGAAGGT GCTCCCAAGA GGGAAGCTTT CCACTAGAGG AGTTCAAATT
GCTTCCAATG AAAATATGGA GACTATGGAA TCAAGTACAC TTGAACTGAG
AAGCAGGTAC TGGGCCATAA GGACCAGAAG TGGAGGAAAC ACCAATCAAC
AGAGGGCATC TGCGGGCCAA ATCAGCATAC AACCTACGTT CTCAGTACAG
AGAAATCTCC CTTTTGACAG AACAACCATT ATGGCAGCAT TCAATGGGAA
TACAGAGGGG AGAACATCTG ACATGAGGAC CGAAATCATA AGGATGATGG
AAAGTGCAAG ACCAGAAGAT GTGTCTTTCC AGGGGCGGGG AGTCTTCGAG
CTCTCGGACG AAAAGGCAGC GAGCCCGATC GTGCCTTCCT TTGACATGAG
TAATGAAGGA TCTTATTTCT TCGGAGACAA TGCAGAGGAG TACGACAATT
AAAGAAAAAT ACCCTTGTTT CTACT
M
AGCAAAAGCA GGTAGATATT GAAAGATGAG TCTTCTAACC GAGGTCGAAA  (SEQ ID NO: 5)
CGTACGTACT CTCTATCATC CCGTCAGGCC CCCTCAAAGC CGAGATCGCA
CAGAGACTTG AAGATGTCTT TGCAGGGAAG AACACCGATC TTGAGGTTCT
CATGGAATGG CTAAAGACAA GACCAATCCT GTCACCTCTG ACTAAGGGGA
TTTTAGGATT TGTGTTCACG CTCACCGTGC CCAGTGAGCG AGGACTGCAG
CGTAGACGCT TTGTCCAAAA TGCCCTTAAT GGGAACGGGG ATCCAAATAA
CATGGACAAA GCAGTTAAAC TGTATAGGAA GCTCAAGAGG GAGATAACAT
TCCATGGGGC CAAAGAAATC TCACTCAGTT ATTCTGCTGG TGCACTTGCC
AGTTGTATGG GCCTCATATA CAACAGGATG GGGGCTGTGA CCACTGAAGT
GGCATTTGGC CTGGTATGTG CAACCTGTGA ACAGATTGCT GACTCCCAGC
ATCGGTCTCA TAGGCAAATG GTGACAACAA CCAATCCACT AATCAGACAT
GAGAACAGAA TGGTTTTAGC CAGCACTACA GCTAAGGCTA TGGAGCAAAT
GGCTGGATCG AGTGAGCAAG CAGCAGAGGC CATGGAGGTT GCTAGTCAGG
```

```
CTAGACAAAT GGTGCAAGCG ATGAGAACCA TTGGGACTCA TCCTAGCTCC

AGTGCTGGTC TGAAAAATGA TCTTCTTGAA AATTTGCAGG CCTATCAGAA

ACGAATGGGG GTGCAGATGC AACGGTTCAA GTGATCCTCT CACTATTGCC

GCAAATATCA TTGGGATCTT GCACTTGACA TTGTGGATTC TTGATCGTCT

TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA

CAGCAGAGTG CTGTGGATGC TGACGATGGT CATTTTGTCA GCATAGAGCT

GGAGTAAAAA ACTACCTTGT TTCTACT
NS
AGCAAAAGCA GGGTGACAAA AACATAATGG ATCCAAACAC TGTGTCAAGC     (SEQ ID NO: 6)

TTTCAGGTAG ATTGCTTTCT TTGGCATGTC CGCAAACGAG TTGCAGACCA

AGAACTAGGC GATGCCCCAT TCCTTGATCG GCTTCGCCGA GATCAGAAAT

CCCTAAGAGG AAGGGGCAGT ACTCTCGGTC TGGACATCAA GACAGCCACA

CGTGCTGGAA AGCAGATAGT GGAGCGGATT CTGAAAGAAG AATCCGATGA

GGCACTTAAA ATGACCATGG CCTCTGTACC TGCGTCGCGT TACCTAACTG

ACATGACTCT TGAGGAAATG TCAAGGGACT GGTCCATGCT CATACCCAAG

CAGAAAGTGG CAGGCCCTCT TTGTATCAGA ATGGACCAGG CGATCATGGA

TAAGAACATC ATACTGAAAG CGAACTTCAG TGTGATTTTT GACCGGCTGG

AGACTCTAAT ATTGCTAAGG GCTTTCACCG AAGAGGGAGC AATTGTTGGC

GAAATTTCAC CATTGCCTTC TCTTCCAGGA CATACTGCTG AGGATGTCAA

AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG

AATGGGAGAC CTCCACTCAC TCCAAAACAG AAACGAGAAA TGGCGGGAAC

AATTAGGTCA GAAGTTTGAA GAAATAAGAT GGTTGATTGA AGAAGTGAGA

CACAAACTGA AGATAACAGA GAATAGTTTT GAGCAAATAA CATTTATGCA

AGCCTTACAT CTATTGCTTG AAGTGGAGCA AGAGATAAGA ACTTTCTCGT

TTCAGCTTAT TTAGTACTAA AAACACCCT TGTTTCTACT
HA
AGCAAAAGCAGGGGAAAATAAAAACAACCAAAATGAAGGCAAACCTACTGGTCC     (SEQ ID NO: 7)

TGTTATGTGCACTTGCAGCTGCAGAT

GCAGACACAATATGTATAGGCTACCATGCGAACAATTCAACCGACACTGTTGAC

ACAGTACTCGAGAAGAATGTGACAGT

GACACACTCTGTTAACCTGCTCGAAGACAGCCACAACGGAAAACTATGTAGATT

AAAAGGAATAGCCCCACTACAATTGG

GGAAATGTAACATCGCCGGATGGCTCTTGGGAAACCCAGAATGCGACCCACTGC

TTCCAGTGAGATCATGGTCCTACATT

GTAGAAACACCAAACTCTGAGAATGGAATATGTTATCCAGGAGATTTCATCGAC

TATGAGGAGCTGAGGGAGCAATTGAG

CTCAGTGTCATCATTCGAAAGATTCGAAATATTTCCCAAAGAAAGCTCATGGCC

CAACCACAACACAAACGGAGTAACGG

CAGCATGCTCCCATGAGGGGAAAAGCAGTTTTTACAGAAATTTGCTATGGCTGA

CGGAGAAGGAGGGCTCATACCCAAAG
```

-continued

CTGAAAAATTCTTATGTGAACAAAAAAGGGAAAGAAGTCCTTGTACTGTGGGGT

ATTCATCACCCGCCTAACAGTAAGGA

ACAACAGAATCTCTATCAGAATGAAAATGCTTATGTCTCTGTAGTGACTTCAAA

TTATAACAGGAGATTTACCCCGGAAA

TAGCAGAAAGACCCAAAGTAAGAGATCAAGCTGGGAGGATGAACTATTACTGGA

CCTTGCTAAAACCCGGAGACACAATA

ATATTTGAGGCAAATGGAAATCTAATAGCACCAATGTATGCTTTCGCACTGAGT

AGAGGCTTTGGGTCCGGCATCATCAC

CTCAAACGCATCAATGCATGAGTGTAACACGAAGTGTCAAACACCCCTGGGAGC

TATAAACAGCAGTCTCCCTTACCAGA

ATATACACCCAGTCACAATAGGAGAGTGCCCAAAATACGTCAGGAGTGCCAAAT

TGAGGATGGTTACAGGACTAAGGAAC

ATTCCGTCCATTCAATCCAGAGGTCTATTTGGAGCCATTGCCGGTTTTATTGAA

GGGGGATGGACTGGAATGATAGATGG

ATGGTATGGTTATCATCATCAGAATGAACAGGGATCAGGCTATGCAGCGGATCA

AAAAAGCACACAAAATGCCATTAACG

GGATTACAAACAAGGTGAACACTGTTATCGAGAAAATGAACATTCAATTCACAG

CTGTGGGTAAAGAATTCAACAAATTA

GAAAAAGGATGGAAAATTTAAATAAAAAAGTTGATGATGGATTTCTGGACATT

TGGACATATAATGCAGAATTGTTAGT

TCTACTGGAAAATGAAAGGACTCTGGATTTCCATGACTCAAATGTGAAGAATCT

GTATGAGAAAGTAAAAAGCCAATTAA

AGAATAATGCCAAAGAAATCGGAAATGGATGTTTTGAGTTCTACCACAAGTGTG

ACAATGAATGCATGGAAAGTGTAAGA

AATGGGACTTATGATTATCCCAAATATTCAGAAGAGTCAAAGTTGAACAGGGAA

AAGGTAGATGGAGTGAAATTGGAATC

AATGGGATCTATCAGATTCTGGCGATCTACTCAACTGTCGCCAGTTCACTGGT

GCTTTTGGTCTCCCTGGGGGCAATCA

GTTTCTGGATGTGTTCTAATGGATCTTTGCAGTGCAGAATATGCATCTGAGATT

AGAATTTCAGAGATATGAGGAAAAAC

ACCCTTGTTTCTACT

NA
AGCAAAAGCAGGGGTTTAAAATGAATCCAAATCAGAAAATAATAACCATTGGAT (SEQ ID NO: 8)

CAATCTGTCTGGTAGTCGGACTAATT

AGCCTAATATTGCAAATAGGGAATATAATCTCAATATGGATTAGCCATTCAATT

CAAACTGGAAGTCAAAACCATACTGG

AATATGCAACCAAAACATCATTACCTATAAAAATAGCACCTGGGTAAAGGACAC

AACTTCAGTGATATTAACCGGCAATT

CATCTCTTTGTCCCATCCGTGGGTGGGCTATATACAGCAAAGACAATAGCATAA

GAATTGGTTCCAAAGGAGACGTTTTT

GTCATAAGAGAGCCCTTTATTTCATGTTCTCACTTGGAATGCAGGACCTTTTTT

-continued

```
CTGACCCAAGGTGCCTTACTGAATGA

CAAGCATTCAAGTGGGACTGTTAAGGACAGAAGCCCTTATAGGGCCTTAATGAG

CTGCCCTGTCGGTGAAGCTCCGTCCC

CGTACAATTCAAGATTTGAATCGGTTGCTTGGTCAGCAAGTGCATGTCATGATG

GCATGGGCTGGCTAACAATCGGAATT

TCAGGTCCAGATAATGGAGCAGTGGCTGTATTAAAATACAACGGCATAATAACT

GAAACCATAAAAAGTTGGAGGAAGAA

AATATTGAGGACACAAGAGTCTGAATGTGCCTGTGTAAATGGTTCATGTTTTAC

TATAATGACTGATGGCCCGAGTGATG

GGCTGGCCTCGTACAAAATTTTCAAGATCGAAAAGGGGAAGGTTACTAAATCAA

TAGAGTTGAATGCACCTAATTCTCAC

TATGAGGAATGTTCCTGTTACCCTGATACCGGCAAAGTGATGTGTGTGTGCAGA

GACAATTGGCATGGTTCGAACCGGCC

ATGGGTGTCTTTCGATCAAAACCTGGATTATCAAATAGGATACATCTGCAGTGG

GGTTTTCGGTGACAACCCGCGTCCCG

AAGATGGAACAGGCAGCTGTGGTCCAGTGTATGTTGATGGAGCAAACGGAGTAA

AGGGATTTTCATATAGGTATGGTAAT

GGTGTTTGGATAGGAAGGACCAAAAGTCACAGTTCCAGACATGGGTTTGAGATG

ATTTGGGATCCTAATGGATGGACAGA

GACTGATAGTAAGTTCTCTGTGAGGCAAGATGTTGTGGCAATGACTGATTGGTC

AGGGTATAGCGGAAGTTTCGTTCAAC

ATCCTGAGCTGACAGGGCTAGACTGTATGAGGCCGTGCTTCTGGGTTGAATTAA

TCAGGGGACGACCTAAAGAAAAAACA

ATCTGGACTAGTGCGAGCAGCATTTCTTTTTGTGGCGTGAATAGTGATACTGTA

GATTGGTCTTGGCCAGACGGTGCTGA

GTTGCCATTCAGCATTGACAAGTAGTCTGTTCAAAAAACTCCTTGTTTCTACT
```

Example 3

Influenza virus A/Hong Kong/213/2003 (H5N1, HK213) replicates systemically in chickens, causing lethal infection. Furthermore, this virus is lethal to chicken embryos. Thus, although its surface proteins are highly related to the currently circulating pathogenic avian influenza viruses, HK213 cannot be used as a vaccine strain as attempts to grow it in embryonated chicken eggs result in the production of poor-quality allantoic fluid. Additionally, the use of this highly virulent virus in the production of vaccines is unsafe for vaccine workers. To test the feasibility of using A/PR/8/34 as a master vaccine strain, the cleavage site of the hemagglutinin (HA) gene of HK213 (containing multiple basic amino acids) was mutated from a virulent to an avirulent phenotype (from RERRRKKR (SEQ ID NO:9) to - - - TETR). A virus containing the mutated HA gene produced non-lethal, localized infection in chickens. Additionally, the mutated virus was non-lethal to chicken embryos. Thus, growth of the mutated virus in embronated eggs yielded high-quality allantoic fluid, and in this attenuated form, the virus is safe for vaccine producers.

A recombinant virus containing the neuraminidase (NA) and mutated HA genes from HK213, and all the remaining genes from high-titer A/PR/8/34 (H1N1, HG-PR8) virus (Example 2), which grows 10 times better than other AIPR/8/34 PR8 strains in eggs ($10^{10}$ $EID_{50}$/ml; HA titer:1:8,000), was generated in embryonated chicken eggs. This recombinant virus, which expresses surface proteins related to the currently circulating pathogenic avian influenza virus, grew to high titers in embryonated chicken eggs (FIG. 4). Thus, replacement of the HA and NA genes of HG-PR8 with those of a currently circulating strain of influenza virus resulted in a vaccine strain that can be safely produced, and demonstrates the use of PR8-HG as a master vaccine strain.

REFERENCES

Avery's Drug Treatment: Principles and Practice of Clinical Pharmacology and Therapeutics, 3rd edition, ADIS Press, Ltd., Williams and Wilkins, Baltimore, Md. (1987).
Aymard-Henry et al., Virology: A Practical Approach, Oxford IRL Press, Oxford, 119-150 (1985).
Bachmeyer, Intervirology, 5:260 (1975).

Berkow et al., eds., *The Merck Manual*, 16th edition, Merck & Co., Rahway, N.J. (1992).
Bridgen et al., *Proc. Natl. Acad. Sci. U.S.A*, 93:15400 (1996).
Castrucci et al., *J. Virol.*, 66:4647 (1992).
Castrucci et al., *J. Virol.*, 69:2725 (1995).
Conzelmann et al., *J. Gen. Virol.*, 77:381 (1996).
Conzelmann et al., *Trends Microbiol.*, 4:386 (1996).
Conzelmann, *Annu. Rev. Genet.*, 32:123 (1998).
Cozelmann et al., *J. Virol.*, 68:713 (1994).
Edwards, *J. Infect. Dis.*, 169: 68 (1994).
Enami et al., *J. Virol.*, 65:2711 (1991).
Enami et al., *Proc. Natl. Acad. Sci. U.S.A.*, 87:3802 (1990).
Enami et al., *Virology*, 185:291 (1991).
Fodor et al., *J. Virol.*, 73:9679 (1999).
Goto et al., *Virology*, 238:265 (1997).
Grand and Skehel, *Nature, New Biology*, 238:145 (1972).
Hatta et al., *Science*, 293:1840 (2001).
Horimoto et al., *J. Virol.*, 68:3120 (1994).
Huddleston et al., *Nucl. Acids Res.*, 10:1029 (1982).
Keitel et al., in Textbook of Influenza, eds. Nickolson, K. G., Webster, R. G., and Hay, A. (Blackwell, Oxford), pp. 373-390 (1998).
Kendal et al., *Infect. Immunity*, 29:966 (1980).
Kilbourne, *Bull. M2 World Health Org.*, 41: 653 (1969).
Kovesdi et al., *J. Curr. Opin. Biotechnol.*, 8:583 (1997).
Laver & Webster, *Virology*, 69:511 (1976).
Lawson et al., *Proc. Natl. Acad. Sci. U.S.A.*, 92:4477 (1995).
Li et al., *Virus Res.*, 37:153 (1995).
Luytjes et al., *Cell*, 59:1107 (1989).
Marriott et al., *Adv. Virus Res.*, 53:321 (1999).
Mena et al., *J. Virol.*, 70:5016 (1996).
Mizrahi, (ed.), *Viral Vaccines*, Wiley-Liss, New York, 39-67 (1990).
Murphy, *Infect. Dis. Clin. Pract.*, 2: 174 (1993).
Muster et al., *Proc. Natl. Acad. Sci. USA*, 88: 5177 (1991).
Munoz et al., *Antiviral Res.*, 46:91 (2000).
Nagai et al., *Microbiol. Immunol.*, 43:613 (1999).
Nagai, *Rev. Med. Virol.*, 9:83 (1999).
Neumann et al., *Adv. Virus Res.*, 53:265 (1999).
Neumann et al., *J. Gen. Virol.*, 83:2635 (2002).
Neumann et al., *J. Virol.*, 71:9690 (1997).
Neumann et al., *Proc. Natl. Acad. Sci. U.S.A*, 96:9345 (1999).
Neumann et al., *Virology*, 202:477 (1994).
Neumann et al., *Virology*, 287:243 (2001).
Niwa et al., *Gene*, 108:193 (1991).
Ogra et al., *J. Infect. Dis.*, 134: 499 (1977).
Osol (ed.), *Remington's Pharmaceutical Sciences*, Mack Publishing Co., Easton, Pa. 1324-1341 (1980).
Parks et al., *J. Virol.*, 73:3560 (1999).
Pekosz et al., *Proc. Natl. Acad. Sci. U.S.A*, 96:8804 (1999).
Perez et al., *Virology*, 242:52 (1998).
Pleschka et al., *J. Virol.*, 70:4188 (1996).
Radecke et al., *EMBO J.*, 14:5773 (1995).
Roberts et al., *Virology*, 247:1 (1998).
Robertson et al., *Biologicals*, 20:213 (1992).
Robertson et al., *Giomale di Igiene e Medicina Preventiva*, 29:4 (1988).
Rose, *Proc. Natl. Acad. Sci. U.S.A*, 93:14998 (1996).
Schnell et al., *EMBO J.*, 13:4195 (1994).
Subbarao et al., *J. Virol.*, 67:7223 (1993).
World Health Organization TSR No. 673 (1982).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed:

1. A plurality of influenza virus vectors for high titer reassortant recombinant influenza virus production comprising:
   a plurality of vectors for vRNA production comprising:
   a vector comprising an influenza virus PA cDNA having SEQ ID NO: 1;
   a vector comprising an influenza virus PB1 cDNA having SEQ ID NO:2;
   a vector comprising an influenza virus PB2 cDNA having SEQ ID NO:3;
   a vector comprising an influenza virus NP cDNA having SEQ ID NO:4;
   a vector comprising an influenza virus M cDNA having SEQ ID NO:5;
   a vector comprising an influenza virus NS cDNA having SEQ ID NO:6;
   a vector comprising an influenza virus H5 HA cDNA; and
   a vector comprising an influenza virus NA cDNA that does not include SEQ ID NO:8,
   wherein each vector for vRNA production further comprises a RNA polymerase I promoter and a RNA polymerase I terminator operably linked to the influenza virus cDNA, and wherein the sequences in the vectors for vRNA production are those for a reassortant influenza virus; and
   a plurality of vectors for mRNA production comprising:
   a vector comprising a promoter operably linked to a DNA segment encoding influenza virus PA;
   a vector comprising a promoter operably linked to a DNA segment encoding influenza virus PB1;
   a vector comprising a promoter operably linked to a DNA segment encoding influenza virus PB2, and
   a vector comprising a promoter operably linked to a DNA segment encoding influenza virus NP.

2. A method to prepare influenza virus, comprising contacting a cell with the plurality of vectors for vRNA production and the plurality of vectors for mRNA production of claim 1, so as to yield an infectious reassortant virus.

3. A plurality of influenza virus for high titer reassortant recombinant influenza virus production comprising:
   a plurality of vectors for vRNA production comprising:
   a vector comprising an influenza virus PA cDNA including sequences that encode a polypeptide encoded by SEQ ID NO: 1;
   a vector comprising an influenza virus PB1 cDNA including sequences that encode a polypeptide encoded by SEQ ID NO:2;
   a vector comprising an influenza virus PB2 cDNA including sequences that encode a polypeptide encoded by SEQ ID NO:3;
   a vector comprising an influenza virus NP cDNA including sequences that encode a polypeptide encoded by SEQ ID NO:4;
   a vector comprising an influenza virus M cDNA including sequences that encode a polypeptide encoded by SEQ ID NO:5;
   a vector comprising an influenza virus NS cDNA including sequences that encode a polypeptide encoded by SEQ ID NO:6;
   a vector comprising an influenza virus H5 HA cDNA; and
   a vector comprising an influenza virus NA cDNA that does not include sequences for a polypeptide encoded by SEQ ID NO:8,
   wherein each vector for vRNA production further comprises a RNA polymerase I promoter and a RNA polymerase I terminator operably linked to the influenza virus cDNA, and wherein the sequences in the vectors for vRNA production are those for a reassortant influenza virus; and
   a plurality of vectors for mRNA production comprising:
   a vector comprising a promoter operably linked to a DNA segment encoding influenza virus PA;
   a vector comprising a promoter operably linked to a DNA segment encoding influenza virus PB1;
   a vector comprising a promoter operably linked to a DNA segment encoding influenza virus PB2, and
   a vector comprising a promoter operably linked to a DNA segment encoding influenza virus NP.

4. A method to prepare influenza virus, comprising contacting a cell with the plurality of vectors for vRNA production and the plurality of vectors for mRNA production of claim 3, so as to yield an infectious reassortant virus.

5. A plurality of influenza virus vectors for high titer reassortant recombinant influenza virus production comprising:
a plurality of vectors for vRNA production comprising:
a vector comprising an influenza virus PA cDNA having SEQ ID NO: 1;
a vector comprising an influenza virus PB1 cDNA having SEQ ID NO:2;
a vector comprising an influenza virus PB2 cDNA having SEQ ID NO:3;
a vector comprising an influenza virus NP cDNA having SEQ ID NO:4;
a vector comprising an influenza virus M cDNA having SEQ ID NO:5;
a vector comprising an influenza virus NS cDNA having SEQ ID NO:6;
a vector comprising an influenza virus NA cDNA that does not include sequences for a polypeptide encoded by SEQ ID NO:7; and
a vector comprising an influenza virus NA cDNA that does not include sequences for a polypeptide encoded by SEQ ID NO:8,
wherein each vector for vRNA production further comprises a RNA polymerase I promoter and a RNA polymerase I terminator operably linked to the influenza virus cDNA, and wherein the sequences in the vectors for vRNA production are those for a reassortant influenza virus; and
a plurality of vectors for mRNA production comprising:
a vector comprising a promoter operably linked to a DNA segment encoding influenza virus PA;
a vector comprising a promoter operably linked to a DNA segment encoding influenza virus PB1;
a vector comprising a promoter operably linked to a DNA segment encoding influenza virus PB2, and
a vector comprising a promoter operably linked to a DNA segment encoding influenza virus NP.

6. A method to prepare influenza virus, comprising contacting a cell with the plurality of vectors for vRNA production and the plurality of vectors for mRNA production of claim 5 so as to yield an infectious reassortant virus.

7. A composition comprising the plurality of vectors of claim 1, 3 or 5.

8. The plurality of vectors of claim 3 or 5 wherein the vectors for mRNA production further include a vector comprising a promoter operably linked to a DNA segment encoding influenza virus HA, a vector comprising a promoter operably linked to a DNA segment encoding influenza virus NA; a vector comprising a promoter operably linked to a DNA segment encoding influenza virus M1, a vector comprising a promoter operably linked to a DNA segment encoding influenza virus M2; or a vector comprising a promoter operably linked to a DNA segment encoding influenza virus NS2.

9. The plurality of vectors of claim 3 or 5 wherein the RNA polymerase I promoter is a human RNA polymerase I promoter.

10. The plurality of vectors of claim 3 or 5 wherein all of the vectors for mRNA production comprise a RNA polymerase II promoter.

11. The plurality of vectors of claim 3 or 5 wherein each vector for vRNA production is on a separate plasmid.

12. The plurality of vectors of claim 3 or 5 wherein each vector for mRNA production is on a separate plasmid.

13. The plurality of vectors of claim 3 or 5 wherein each of the vectors for mRNA production further comprise a RNA transcription termination sequence.

14. The plurality of vectors of claim 3 or 5 further comprising a vector comprising a promoter linked to 5' influenza virus sequences comprising 5' influenza virus noncoding sequences linked to a cDNA of interest linked to 3' influenza virus sequences comprising 3' influenza virus noncoding sequences linked to a transcription termination sequence.

15. The plurality of vectors of claim 14 wherein the cDNA of interest is in the sense orientation.

16. The plurality of vectors of claim 14 wherein the cDNA of interest is in the antisense orientation.

17. The plurality of vectors of claim 14 wherein the cDNA or interest comprises an open reading frame encoding an immunogenic polypeptide or peptide of a pathogen or a therapeutic polypeptide or peptide.

18. The method of claim 4 or 6 further comprising isolating the virus.

19. A method to prepare a gene delivery vehicle, comprising: contacting cells with the plurality of vectors of claim 14 in an amount effective to yield influenza virus, and isolating the virus.

20. An isolated virus obtained by the method of claim 19.

21. An isolated cell contacted with the plurality of vectors of claim 3 or 5.

22. An isolated cell infected with the virus of claim 20.

23. The method of claim 4 or 6 further comprising a vector comprising a promoter operably linked to a DNA segment encoding influenza, virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, and a vector comprising a promoter operably linked to a DNA segment encoding influenza virus NS2.

24. The method of claim 23 further comprising a vector comprising a promoter linked to 5' influenza virus sequences comprising 5' influenza virus noncoding sequences linked to a cDNA of interest or a fragment thereof linked to 3' influenza virus sequences comprising 3' influenza virus noncoding sequences linked to a transcription termination sequence.

25. The method of claim 24 wherein the cDNA of interest comprises an open reading frame encoding an immunogenic polypeptide or peptide of a pathogen or a therapeutic polypeptide or peptide.

26. The method of claim 24 wherein the cDNA of interest is in the sense orientation.

27. The method of claim 24 wherein the cDNA of interest is in the antisense orientation.

28. The method of claim 4 or 6 further comprising isolating the virus.

29. The plurality of vectors of claim 3 wherein the cDNA for PA, PB1, PB2, NP, M and NS has at least 90% nucleotide sequence identity to SEQ ID NOs:1-6 or the complement thereof.

30. The method of claim 4 wherein the cDNA for PA, PB1, PB2, NP, M and NS has at least 90% nucleotide sequence identity to SEQ ID NOs:1-6 or the complement thereof.

31. The plurality of vectors of claim 1 or 3 wherein the H5 HA is a mutant H5 with an avirulent cleavage site.

32. The method of claim 2 or 4 wherein the cDNA for H5 HA is a mutant H5 with an avirulent cleavage site.

* * * * *

UNITED STATES PATENT AND TRADEMARK OFFICE
CERTIFICATE OF CORRECTION

PATENT NO.         : 8,475,806 B2                                         Page 1 of 11
APPLICATION NO.    : 10/855875
DATED              : July 2, 2013
INVENTOR(S)        : Yoshihiro Kawaoka It is certified that error appears in the above-identified patent and that said Letters Patent is hereby corrected as shown below:

On the Title page, in column 2, Item (56) under "Other Publications", line 1, delete "No. 3" and insert --No:3--, therefor On the Title page, in column 2, Item (56) under "Other Publications", line 2, delete "No. 4" and insert --No:4--, therefor On the Title page, in column 2, Item (56) under "Other Publications", line 4, delete "No. 5" and insert --No:5--, therefor On the Title page, in column 2, Item (56) under "Other Publications", line 5, delete "No. 6" and insert --No:6--, therefor On the Title page, in column 2, Item (56) under "Other Publications", line 8, delete "candidate, "" and insert --candidate,"--, therefor On the Title page, in column 2, Item (56) under "Other Publications", line 13, delete "No. 2" and insert --No:2--, therefor On the Title page, in column 2, Item (56) under "Other Publications", line 22, before "Generation", insert --"--, therefor On the Title page, in column 2, Item (56) under "Other Publications", line 23, after "candidate", insert --"--, therefor On the Title page, in column 2, Item (56) under "Other Publications", line 44, delete "96.(1999),9345-9350" and insert --96,(1999), 9345-9350--, therefor On Title page 2, in column 1, Item (56) under "Other Publications", line 2, delete "Virology74(1)," and insert --Virol., 74(1),--, therefor <div style="text-align: center;">
Signed and Sealed this
Seventeenth Day of February, 2015

Michelle K. Lee
*Deputy Director of the United States Patent and Trademark Office*
</div>

CERTIFICATE OF CORRECTION (continued)
U.S. Pat. No. 8,475,806 B2

On Title page 2, in column 1, Item (56) under "Other Publications", line 7, delete "K. ," and insert --K.,--, therefor On Title page 2, in column 1, Item (56) under "Other Publications", line 12, delete "(1992),417-428" and insert --(1992), 417-428--, therefor On Title page 2, in column 1, Item (56) under "Other Publications", line 14, delete "(1997),1265-1271" and insert --(1997), 1265-1271--, therefor On Title page 2, in column 1, Item (56) under "Other Publications", line 17, delete "(1975),729-732" and insert --(1975), 729-732--, therefor On Title page 2, in column 1, Item (56) under "Other Publications", line 19, after "198", insert --,--, therefor On Title page 2, in column 1, Item (56) under "Other Publications", line 19, delete "(1994),415-426" and insert --(1994), 415-426--, therefor On Title page 2, in column 1, Item (56) under "Other Publications", line 22, delete "(1996),15400-15404" and insert --(1996), 15400-15404--, therefor On Title page 2, in column 1, Item (56) under "Other Publications", line 30, delete "70(10))" and insert --70(10)--, therefor On Title page 2, in column 1, Item (56) under "Other Publications", line 33, delete "(1995),2725-" and insert --(1995), 2725- --, therefor On Title page 2, in column 1, Item (56) under "Other Publications", line 37, delete "(1999),2273-2283" and insert --(1999), 2273-2283--, therefor On Title page 2, in column 1, Item (56) under "Other Publications", line 39, delete "(2000),4831-4838" and insert --(2000), 4831-4838--, therefor On Title page 2, in column 1, Item (56) under "Other Publications", line 48, delete "(1995),11563-11567" and insert --(1995), 11563-11567--, therefor On Title page 2, in column 1, Item (56) under "Other Publications", line 52, delete "(1991),9663-9667" and insert --(1991), 9663-9667--, therefor On Title page 2, in column 1, Item (56) under "Other Publications", line 54, delete "(1996),386-393" and insert --(1996), 386-393--, therefor On Title page 2, in column 1, Item (56) under "Other Publications", line 56, after "77", insert --,--, therefor CERTIFICATE OF CORRECTION (continued)
U.S. Pat. No. 8,475,806 B2

On Title page 2, in column 1, Item (56) under "Other Publications", line 57, delete "(1996),381-389" and insert --(1996), 381-389--, therefor On Title page 2, in column 1, Item (56) under "Other Publications", line 60, delete "(1998),123-162" and insert --(1998), 123-162--, therefor On Title page 2, in column 1, Item (56) under "Other Publications", line 63, delete "(1994),713-719" and insert --(1994), 713-719--, therefor On Title page 2, in column 1, Item (56) under "Other Publications", line 67, delete "(1985),40-49" and insert --(1985), 40-49--, therefor On Title page 2, in column 1, Item (56) under "Other Publications", line 69, delete "(1993),344-348" and insert --(1993), 344-348--, therefor On Title page 2, in column 1, Item (56) under "Other Publications", line 71, delete "(1994),367-375" and insert --(1994), 367-375--, therefor On Title page 2, in column 1, Item (56) under "Other Publications", line 72, delete "S. ," and insert --S.,--, therefor On Title page 2, in column 2, Item (56) under "Other Publications", line 4, delete "(1993),535-539" and insert --(1993), 535-539--, therefor On Title page 2, in column 2, Item (56) under "Other Publications", line 7, delete "(1995),2427-2435" and insert --(1995), 2427-2435--, therefor On Title page 2, in column 2, Item (56) under "Other Publications", line 10, delete "(1993),2772-2778" and insert --(1993), 2772-2778--, therefor On Title page 2, in column 2, Item (56) under "Other Publications", line 14, delete "(1988),31-40" and insert --(1988), 31-40--, therefor On Title page 2, in column 2, Item (56) under "Other Publications", line 17, delete "(1995),133-143" and insert --(1995), 133-143--, therefor On Title page 2, in column 2, Item (56) under "Other Publications", line 19, delete "(1997),323-332" and insert --(1997), 323-332--, therefor On Title page 2, in column 2, Item (56) under "Other Publications", line 24, delete "(1991),1761-1779" and insert --(1991), 1761-1779--, therefor On Title page 2, in column 2, Item (56) under "Other Publications", line 27, delete "(1975),1348-1356" and insert --(1975), 1348-1356--, therefor

CERTIFICATE OF CORRECTION (continued)
U.S. Pat. No. 8,475,806 B2

On Title page 2, in column 2, Item (56) under "Other Publications", line 29, delete "(1991),291-298" and insert --(1991), 291-298--, therefor On Title page 2, in column 2, Item (56) under "Other Publications", line 31, delete "(1991),2711-2713" and insert --(1991), 2711-2713--, therefor On Title page 2, in column 2, Item (56) under "Other Publications", line 34, delete "(1990),3802-3805" and insert --(1990), 3802-3805--, therefor On Title page 2, in column 2, Item (56) under "Other Publications", line 37, delete "(1992),1-5" and insert --(1992), 1-5--, therefor On Title page 2, in column 2, Item (56) under "Other Publications", line 38, delete "P. ," and insert --P.,--, therefor On Title page 2, in column 2, Item (56) under "Other Publications", line 40, delete "(1994),704-712" and insert --(1994), 704-712--, therefor On Title page 2, in column 2, Item (56) under "Other Publications", line 42, delete "(1993),765-790" and insert --(1993), 765-790--, therefor On Title page 2, in column 2, Item (56) under "Other Publications", line 42, delete "(1993),765-790" and insert --(1993), 765-790--, therefor On Title page 2, in column 2, Item (56) under "Other Publications", line 43, delete "D. ," and insert --D.,--, therefor On Title page 2, in column 2, Item (56) under "Other Publications", line 46, delete "(1995),6087-6094" and insert --(1995), 6087-6094--, therefor On Title page 2, in column 2, Item (56) under "Other Publications", line 49, delete "(1997),265-272" and insert --(1997), 265-272--, therefor On Title page 2, in column 2, Item (56) under "Other Publications", line 54, delete "(1995),5677-5686" and insert --(1995), 5677-5686--, therefor On Title page 2, in column 2, Item (56) under "Other Publications", line 55, delete "E. ," and insert --E.,--, therefor On Title page 2, in column 2, Item (56) under "Other Publications", line 56, delete "1992 ,3325-3329" and insert --1992, 3325-3329--, therefor On Title page 2, in column 2, Item (56) under "Other Publications", line 57, delete "B. ," and insert --B.,--, therefor

CERTIFICATE OF CORRECTION (continued)
U.S. Pat. No. 8,475,806 B2

On Title page 2, in column 2, Item (56) under "Other Publications", line 58, delete "(1997),249-260" and insert --(1997), 249-260--, therefor On Title page 2, in column 2, Item (56) under "Other Publications", line 60, delete "(1997),4272-4277" and insert --(1997), 4272-4277--, therefor On Title page 2, in column 2, Item (56) under "Other Publications", line 63, delete "(2000),310-317" and insert --(2000), 310-317--, therefor On Title page 2, in column 2, Item (56) under "Other Publications", line 66, delete "(1990),5669-5673" and insert --(1990), 5669-5673--, therefor On Title page 2, in column 2, Item (56) under "Other Publications", line 68, delete "(1985),8824-8428" and insert --(1985), 8824-8428--, therefor On Title page 2, in column 2, Item (56) under "Other Publications", line 70, delete "(1997),315" and insert --(1997), 315--, therefor On Title page 3, in column 1, Item (56) under "Other Publications", line 3, delete "(1996),569-579" and insert --(1996), 569-579--, therefor On Title page 3, in column 1, Item (56) under "Other Publications", line 10, delete "73,(1992),1321-1328" and insert --73, (1992), 1321-1328--, therefor On Title page 3, in column 1, Item (56) under "Other Publications", line 11, delete "M. ," and insert --M.,--, therefor On Title page 3, in column 1, Item (56) under "Other Publications", line 13, delete "(1992),235-245" and insert --(1992), 235-245--, therefor On Title page 3, in column 1, Item (56) under "Other Publications", line 15, delete "(1990),609-618" and insert --(1990), 609-618--, therefor On Title page 3, in column 1, Item (56) under "Other Publications", line 18, delete "(1986),2709-" and insert --(1986), 2709- --, therefor On Title page 3, in column 1, Item (56) under "Other Publications", line 22, delete "(1985),488-492" and insert --(1985), 488-492--, therefor On Title page 3, in column 1, Item (56) under "Other Publications", line 32, delete "(1995),4477-4481" and insert --(1995), 4477-4481.--, therefor On Title page 3, in column 1, Item (56) under "Other Publications", line 35, delete "(1986),137-145" and insert --(1986), 137-145--, therefor On Title page 3, in column 1, Item (56) under "Other Publications", line 37, delete "(1989),1107-1113" and insert --(1989), 1107-1113--, therefor On Title page 3, in column 1, Item (56) under "Other Publications", line 38, delete "I. ," and insert --I.,--, therefor On Title page 3, in column 1, Item (56) under "Other Publications", line 40, delete "1996),5016-5024" and insert --1996), 5016-5024--, therefor On Title page 3, in column 1, Item (56) under "Other Publications", line 43, delete "(1994),2109-2114" and insert --(1994), 2109-2114--, therefor On Title page 3, in column 1, Item (56) under "Other Publications", line 46, delete "(1991),2170-2178" and insert --(1991), 2170-2178--, therefor On Title page 3, in column 1, Item (56) under "Other Publications", line 50, delete "(Jun. 1991),5177-5181" and insert --(Jun. 1991), 5177-5181--, therefor On Title page 3, in column 1, Item (56) under "Other Publications", line 51, delete "S. ," and insert --S.,--, therefor On Title page 3, in column 1, Item (56) under "Other Publications", line 53, delete "(1976),4307-4314" and insert --(1976), 4307-4314--, therefor On Title page 3, in column 1, Item (56) under "Other Publications", line 57, delete "(1987),283-302" and insert --(1987), 283-302--, therefor On Title page 3, in column 1, Item (56) under "Other Publications", line 60, delete "(1998),991-1000" and insert --(1998), 991-1000--, therefor On Title page 3, in column 1, Item (56) under "Other Publications", line 62, delete "(Jul. 1994),477-479" and insert --(Jul. 1994), 477-479--, therefor On Title page 3, in column 1, Item (56) under "Other Publications", line 64, delete "USA,93(21),(1996),11354-11358" and insert --USA, 93(21), (1996), 11354- --, therefor On Title page 3, in column 1, Item (56) under "Other Publications", line 67, delete "(1991),5537-5541" and insert --(1991), 5537-5541--, therefor On Title page 3, in column 1, Item (56) under "Other Publications", line 71, delete "(1991),1379-1383" and insert --(1991), 1379-1383--, therefor On Title page 3, in column 1, Item (56) under "Other Publications", line 75, delete "(1999),5001-5009" and insert --(1999), 5001-5009--, therefor

CERTIFICATE OF CORRECTION (continued)
U.S. Pat. No. 8,475,806 B2

On Title page 3, in column 1, Item (56) under "Other Publications", line 78, delete "(1999),8804-8806" and insert --(1999), 8804-8806--, therefor On Title page 3, in column 2, Item (56) under "Other Publications", line 2, delete "(1994),4486-4492" and insert --(1994), 4486-4492--, therefor On Title page 3, in column 2, Item (56) under "Other Publications", line 4, delete "(Jun. 1996),4188-4192" and insert --(Jun. 1996), 4188-4192--, therefor On Title page 3, in column 2, Item (56) under "Other Publications", line 5, delete "Y. ," and insert --Y.,--, therefor On Title page 3, in column 2, Item (56) under "Other Publications", line 7, delete "(1995),304-316" and insert --(1995), 304-316--, therefor On Title page 3, in column 2, Item (56) under "Other Publications", line 8, delete "Y. ," and insert --Y.,--, therefor On Title page 3, in column 2, Item (56) under "Other Publications", line 10, delete "(1994),2425-2432" and insert --(1994), 2425-2432--, therefor On Title page 3, in column 2, Item (56) under "Other Publications", line 13, delete "F. ," and insert --F.,--, therefor On Title page 3, in column 2, Item (56) under "Other Publications", line 14, delete "(1995),5773-5784" and insert --(1995), 5773-5784--, therefor On Title page 3, in column 2, Item (56) under "Other Publications", line 15, delete "F. ," and insert --F.,--, therefor On Title page 3, in column 2, Item (56) under "Other Publications", line 17, delete "(1997),49-63" and insert --(1997), 49-63--, therefor On Title page 3, in column 2, Item (56) under "Other Publications", line 18, delete "A. ," and insert --A.,--, therefor On Title page 3, in column 2, Item (56) under "Other Publications", line 20, delete "(1998),1-6" and insert --(1998), 1-6--, therefor On Title page 3, in column 2, Item (56) under "Other Publications", line 23, delete "(1996),14998-15000" and insert --(1996), 14998-15000--, therefor On Title page 3, in column 2, Item (56) under "Other Publications", line 25, delete "(1995),155-" and insert --(1995), 155- --, therefor On Title page 3, in column 2, Item (56) under "Other Publications", line 28, delete "(1994),4195-4203" and insert --(1994), 4195-4203--, therefor On Title page 3, in column 2, Item (56) under "Other Publications", line 32, delete "(1992),247-260" and insert --(1992), 247-260--, therefor On Title page 3, in column 2, Item (56) under "Other Publications", line 35, delete "(1995),800-" and insert --(1995), 800- --, therefor On Title page 3, in column 2, Item (56) under "Other Publications", line 42, delete "(1995),5969-5977" and insert --(1995), 5969-5977--, therefor On Title page 3, in column 2, Item (56) under "Other Publications", line 45, delete "(1988),7907-7911" and insert --(1988), 7907-7911--, therefor On Title page 3, in column 2, Item (56) under "Other Publications", line 48, delete "(1990),1441-1450" and insert --(1990), 1441-1450--, therefor On Title page 3, in column 2, Item (56) under "Other Publications", line 51, delete "(1988),558-562" and insert --(1988), 558-562--, therefor On Title page 3, in column 2, Item (56) under "Other Publications", line 54, delete "(1995),8388-8392" and insert --(1995), 8388-8392--, therefor On Title page 3, in column 2, Item (56) under "Other Publications", line 55, delete "K. ," and insert --K.,--, therefor On Title page 3, in column 2, Item (56) under "Other Publications", line 57, delete "(1991),5369" and insert --(1991), 5369--, therefor On Title page 3, in column 2, Item (56) under "Other Publications", line 63, delete "(1995),2412-2419" and insert --(1995), 2412-2419--. therefor On Title page 3, in column 2, Item (56) under "Other Publications", line 66, delete "(1987),3961-" and insert --(1987), 3961--, therefor On Title page 3, in column 2, Item (56) under "Other Publications", line 68, delete "H. ," and insert --H.,--, therefor On Title page 3, in column 2, Item (56) under "Other Publications", line 70, delete "(1992),3604-3609" and insert --(1992), 3604-3609--, therefor On Title page 4, in column 1, Item (56) under "Other Publications", line 1, delete "H. ," and insert --H.,--, therefor On Title page 4, in column 1, Item (56) under "Other Publications", line 4, delete "(1991),5645-5649" and insert --(1991), 5645-5649--, therefor On Title page 4, in column 1, Item (56) under "Other Publications", line 5, delete "H. ," and insert --H.,--, therefor On Title page 4, in column 1, Item (56) under "Other Publications", line 8, delete "(1994),95-101" and insert --(1994), 95-101--, therefor On Title page 4, in column 1, Item (56) under "Other Publications", line 9, delete "A. ," and insert --A.,--, therefor On Title page 4, in column 1, Item (56) under "Other Publications", line 10, delete "(1993),3607-" and insert --(1993), 3607- --, therefor On Title page 4, in column 1, Item (56) under "Other Publications", line 12, delete "Y. ," and insert --Y.,--, therefor On Title page 4, in column 1, Item (56) under "Other Publications", line 15, delete "ERTR,8" and insert --ERTR, 8--, therefor On Title page 4, in column 1, Item (56) under "Other Publications", line 17, delete "ERTR-1,2" and insert --ERTR-1, 2--, therefor On Title page 4, in column 1, Item (56) under "Other Publications", line 19, delete "8-06-08" and insert --Aug. 06, 2008--, therefor On Title page 4, in column 1, Item (56) under "Other Publications", line 19, delete "FOOAR-MISC,5" and insert --FOOAR-MISC, 5--, therefor On Title page 4, in column 1, Item (56) under "Other Publications", line 69, delete "mailed" and insert --filed--, therefor On Title page 4, in column 2, Item (56) under "Other Publications", line 6, delete "Mailed" and insert --mailed--, therefor On Title page 4, in column 2, Item (56) under "Other Publications", line 26, after "200480021259.9", insert --,--, therefor On Title page 4, in column 2, Item (56) under "Other Publications", line 28, delete "PA/a/2005/012712 ,Office" and insert --PA/a/2005/012712, Office--, therefor On Title page 4, in column 2, Item (56) under "Other Publications", line 29, delete "Mailed" and insert --mailed--, therefor On Title page 4, in column 2, Item (56) under "Other Publications", line 30, after "PA/a/2005/012712", insert --,--, therefor On Title page 4, in column 2, Item (56) under "Other Publications", line 30, delete "Action-" and insert --Action--, therefor On Title page 4, in column 2, Item (56) under "Other Publications", line 32, before ""Chinese", delete "200480021259.9,", therefor On Title page 4, in column 2, Item (56) under "Other Publications", line 34, before ""Eurasian", delete "200501890,", therefor On Title page 4, in column 2, Item (56) under "Other Publications", line 36, before ""Ukrainese", delete "200512619,", therefor On Title page 4, in column 2, Item (56) under "Other Publications", line 36, delete "200512619 ," and insert --200512619,--, therefor On Title page 4, in column 2, Item (56) under "Other Publications", line 43, after "6", insert --.--, therefor On Title page 4, in column 2, Item (56) under "Other Publications", line 50, delete "Filed" and insert --filed--, therefor On Title page 4, in column 2, Item (56) under "Other Publications", line 52, after "533439", insert --,--, therefor On Title page 4, in column 2, Item (56) under "Other Publications", line 54, delete "200480021259.9 ," and insert --200480021259.9,--, therefor On Title page 4, in column 2, Item (56) under "Other Publications", line 59, delete "Response to Office Action", therefor On Title page 4, in column 2, Item (56) under "Other Publications", line 62, delete "Maxican application serial No. PA/a/2005/012712 , office action" and insert --Mexican Application Serial No. PA/a/2005/012712, Office Action--, therefor On Title page 4, in column 2, Item (56) under "Other Publications", line 64, delete "Maxican application serial No. PA/a/2005/012712 , office action" and insert --Mexican Application Serial No. PA/a/2005/012712, Office Action--, therefor On Title page 4, in column 2, Item (56) under "Other Publications", line 70, delete "received" and insert --mailed--, therefor

CERTIFICATE OF CORRECTION (continued)
U.S. Pat. No. 8,475,806 B2

On Title page 5, in column 1, Item (56) under "Other Publications", line 11, after "2010", insert --,--, therefor On Title page 5, in column 1, Item (56) under "Other Publications", line 14, after "200480021259.9", insert --,--, therefor On Title page 5, in column 1, Item (56) under "Other Publications", line 15, delete "Filed" and insert --filed--, therefor On Title page 5, in column 1, Item (56) under "Other Publications", line 18, delete "2006-533439,Office" and insert --2006-533439, Office--, therefor On Title page 5, in column 1, Item (56) under "Other Publications", line 22, delete "PA/a/2005/012712 ," and insert --PA/a/2005/012712,--, therefor On Title page 5, in column 1, Item (56) under "Other Publications", line 23, delete "Filed" and insert --filed--, therefor On Title page 5, in column 2, Item (56) under "Other Publications", line 1, delete "H," and insert --H.,--, therefor On Title page 5, in column 2, Item (56) under "Other Publications", line 20, delete "Claims)." and insert --Claims),--, therefor On Title page 5, in column 2, Item (56) under "Other Publications", line 9, delete "Oct. 16, 12" and insert --Oct. 16, 2012--, therefor In the Claims In column 63, line 31, in Claim 1, delete "NO: 1" and insert --NO:1--, therefor In column 64, line 31, in Claim 3, delete "NO: 1" and insert --NO:1--, therefor In column 65, line 8, in Claim 5, delete "NO: 1" and insert --NO:1--, therefor In column 66, line 16, in Claim 17, delete "or" and insert --of--, therefor In column 66, line 31, in Claim 23, delete "influenza," and insert --influenza--, therefor

UNITED STATES PATENT AND TRADEMARK OFFICE
CERTIFICATE OF CORRECTION

PATENT NO. : 8,475,806 B2  
APPLICATION NO. : 10/855875  
DATED : July 2, 2013  
INVENTOR(S) : Yoshihiro Kawaoka Page 1 of 1

It is certified that error appears in the above-identified patent and that said Letters Patent is hereby corrected as shown below:

In the Specification

Column 1, Lines 15-19:
Delete the phrase:
"This invention was made with a grant from the Government of the United States of America (grant AI-47446 from the National Institute of Allergy and Infectious Diseases Public Health Service). The Government may have certain rights in the invention."

And replace with:
--This invention was made with government support under AI047446 awarded by the National Institutes of Health. The government has certain rights in the invention.--.

Signed and Sealed this  
First Day of December, 2020

Andrei Iancu  
*Director of the United States Patent and Trademark Office*

```
                        SEQUENCE LISTING

<160> NUMBER OF SEQ ID NOS: 40

<210> SEQ ID NO 1
<211> LENGTH: 2233
<212> TYPE: DNA
<213> ORGANISM: Influenza virus

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gattcatcga aattggagta acaaggagag aagttcacat atactatctg     420
gaaaaggcca ataaaattaa atctgagaaa acacacatcc acattttctc gttcactggg     480
gaagaaatgg ccacaaaggc agactacact ctcgatgaag aaagcagggc taggatcaaa     540
accagactat tcaccataag acaagaaatg gccagcagag gcctctggga ttcctttcgt     600
cagtccgaga gaggagaaga gacaattgaa gaaaggtttg aaatcacagg aacaatgcgc     660
aagcttgccg accaaagtct cccgccgaac ttctccagcc ttgaaaattt tagagcctat     720
```

```
gtggatggat cgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag agatatgct tataagaagt   1680 gccataggcc aggttttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat caacagctt gtatgcatct   1980 ccacaactag aaggattttc agctgaatca agaaaactgc ttcttatcgt tcaggctctt   2040
agggacaacc tggaacctgg gacctttgat cttggggggc tatatgaagc aattgaggag   2100
tgcctgatta atgatcctg ggttttgctt aatgcttctt ggttcaactc cttccttaca   2160
catgcattga gttagttgtg gcagtgctac tatttgctat ccatactgtc caaaaaagta   2220
ccttgtttct act                                                       2233
```

<210> SEQ ID NO 2
<211> LENGTH: 2341
<212> TYPE: DNA
<213> ORGANISM: Influenza virus

<400> SEQUENCE: 2

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta tcagaaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga acgatggag     360 gttgttcagc aaacacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca agaagaaat ggggatcaca actcattttc agagaaagag acgggtgaga    600
```

```
gacaatatga ctaagaaaat gataacacag agaacaatgg gtaaaaagaa gcagagattg    660
aacaaaagga gttatctaat tagagcattg accctgaaca caatgaccaa agatgctgag    720
agagggaagc taaaacggag agcaattgca accccaggga tgcaaataag gggtttgta     780 tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata acaccaaatg gaacgaaaat    960
cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca tcgatttgaa atatttcaat gattcaacaa gaaagaagat tgaaaaaatc   1200
cgaccgctct taatagaggg gactgcatca ttgagccctg gaatgatgat gggcatgttc   1260
aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga atacaagtca aagaggagta cttgaggatg aacaaatgta ccaaaggtgc   2100
tgcaatttat ttgaaaaatt cttccccagc agttcataca gaagaccagt cgggatatcc   2160
agtatggtgg aggctatggt ttccagagcc cgaattgatg cacggattga tttcgaatct   2220
ggaaggataa agaaagaaga gttcactgag atcatgaaga tctgttccac cattgaagag   2280
ctcagacggc aaaaatagtg aatttagctt gtccttcatg aaaaaatgcc ttgtttctac   2340
t                                                                   2341

<210> SEQ ID NO 3
<211> LENGTH: 2341
<212> TYPE: DNA
<213> ORGANISM: Influenza virus

<400> SEQUENCE: 3
agcgaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
```

| | |
|---|---:|
| ccaaaaatct acaaaactta ttttgaaaga gtcgaaaggc taaagcatgg aacctttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg gaagtgagg | 780 |
| aatgatgatg ttgatcaaag cttgattatt gctgctagga acatagtgag aagagctgca | 840 |
| gtatcagcag atccactagc atctttattg gagatgtgcc acagcacaca gattggtgga | 900 |
| attaggatgg tagacatcct taggcagaac ccaacagaag agcaagccgt ggatatatgc | 960 |
| aaggctgcaa tgggactgag aattagctca tccttcagtt ttggtggatt cacatttaag | 1020 |
| agaacaagcg gatcatcagt caagagagag aagaggtgc ttacgggcaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtca gaggtgatct gaatttcgtc aataggcga atcaacgatt gaatcctatg | 1320 |
| catcaacttt taagacattt tcagaaggat gcgaaagtgc ttttttcaaaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaatgggtg tagatgagta ctccagcacg | 1500 |
| gagagggtag tggtgagcat tgaccgtttt ttgagaatcc gggaccaacg aggaaatgta | 1560 |
| ctactgtctc ccgaggaggt cagtgaaaca cagggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtaagaac tctgttccaa caaatgaggg atgtgcttgg acatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaaggggc | 1980 |
| aattctcctg tattcaacta taacaaggcc acgaagagac tcacagttct cggaaaggat | 2040 |
| gctggcactt taactgaaga cccagatgaa ggcacagctg gagtggagtc cgctgttctg | 2100 |
| agggattcc tcattctggg caagaagac aagagatatg gccagcact aagcatcaat | 2160 |
| gaactgagca accttgcgaa aggagagaag gctaatgtgc taattgggca aggagacgtg | 2220 |
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 4
<211> LENGTH: 1565
<212> TYPE: DNA
<213> ORGANISM: Influenza virus

<400> SEQUENCE: 4

| | |
|---|---:|
| agcaaaagca gggtagataa tcactcactg agtgacatca aaatcatggc gtctcaaggc | 60 |
| accaaacgat cttacgaaca gatggagact gatggagaac gccagaatgc cactgaaatc | 120 |

-continued

```
agagcatccg tcggaaaaat gattggtgga attggacgat tctacatcca aatgtgcacc    180
gaactcaaac tcagtgatta tgagggacgg ttgatccaaa acagcttaac aatagagaga    240
atggtgctct ctgcttttga cgaaaggaga aataaatacc ttgaagaaca tcccagtgcg    300
gggaaagatc ctaagaaaac tggaggacct atatacagga gagtaaacgg aaagtggatg    360
agagaactca tcctttatga caagaagaa ataaggcgaa tctggcgcca agctaataat    420
ggtgacgatg caacggctgg tctgactcac atgatgatct ggcattccaa tttgaatgat    480
gcaacttatc agaggacaag agctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcaga atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag gaatgctgga ttcgaagat ctcacttttc tagcacggtc tgcactcata    840
ttgagagggt cggttgctca caagtcctgc ctgcctgcct gtgtgtatgg acctgccgta    900
gccagtgggt acgactttga aagggaggga tactctctag tcggaataga ccctttcaga    960
ctgcttcaaa acagccaagt gtacagccta atcagaccaa atgagaatcc agcacacaag   1020
agtcaactgg tgtggatggc atgccattct gccgcatttg aagatctaag agtattaagc   1080
ttcatcaaag gacgaaggt gctcccaaga gggaagcttt ccactagagg agttcaaatt   1140
gcttccaatg aaaatatgga gactatgaa tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccatt   1320
atggcagcat tcaatgggaa tacagagggg agaacatctg acatgaggac cgaaatcata   1380
aggatgatgg aaagtgcaag accagaagat gtgtctttcc aggggcgggg agtcttcgag   1440
ctctcggacg aaaaggcagc gagcccgatc gtgccttcct ttgacatgag taatgaagga   1500
tcttatttct tcggagacaa tgcagaggag tacgacaatt aaagaaaaat acccttgttt   1560
ctact                                                               1565
```

<210> SEQ ID NO 5
<211> LENGTH: 1027
<212> TYPE: DNA
<213> ORGANISM: Influenza virus

<400> SEQUENCE: 5

```
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg cctcatata    420 caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
```

-continued

```
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca ttgggatctt gcacttgaca ttgtggattc    840
ttgatcgtct ttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                             1027
```

<210> SEQ ID NO 6
<211> LENGTH: 890
<212> TYPE: DNA
<213> ORGANISM: Influenza virus

<400> SEQUENCE: 6

```
agcaaaagca gggtgacaaa aacataatgg atccaaacac tgtgtcaagc tttcaggtag     60
attgctttct ttggcatgtc cgcaaacgag ttgcagacca agaactaggc gatgccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact               890
```

<210> SEQ ID NO 7
<211> LENGTH: 1775
<212> TYPE: DNA
<213> ORGANISM: Influenza virus

<400> SEQUENCE: 7

```
agcaaaagca ggggaaaata aaaacaacca aaatgaaggc aaacctactg gtcctgttat     60
gtgcacttgc agctgcagat gcagacacaa tatgtatagg ctaccatgcg aacaattcaa    120
ccgacactgt tgacacagta ctcgagaaga atgtgacagt gacacactct gttaacctgc    180
tcgaagacag ccacaacgga aaactatgta gattaaaagg aatagcccca ctacaattgg    240
ggaaatgtaa catcgccgga tggctcttgg gaaacccaga atgcgaccca ctgcttccag    300
tgagatcatg gtcctacatt gtagaaacac caaactctga gaatggaata tgttatccag    360
gagatttcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa tttgctatgg ctgacggaga    540
aggagggctc atacccaaag ctgaaaaatt cttatgtgaa caaaaaaggg aaagaagtcc    600
```

```
ttgtactgtg gggtattcat cacccgccta acagtaagga acaacagaat ctctatcaga    660
atgaaaatgc ttatgtctct gtagtgactt caaattataa caggagattt accccggaaa    720
tagcagaaag acccaaagta agagatcaag ctgggaggat gaactattac tggaccttgc    780
taaaacccgg agacacaata atatttgagg caaatggaaa tctaatagca ccaatgtatg    840
ctttcgcact gagtagaggc tttggtccg  catcatcac ctcaaacgca tcaatgcatg    900
agtgtaacac gaagtgtcaa acaccctgg  gagctataaa cagcagtctc ccttaccaga    960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaaggggga tggactggaa tgatagatgg atggtatggt tatcatcatc   1140
agaatgaaca gggatcaggc tatgcagcgg atcaaaaaag cacacaaaat gccattaacg   1200
ggattacaaa caaggtgaac actgttatcg agaaaatgaa cattcaattc acagctgtgg   1260
gtaaagaatt caacaaatta gaaaaaagga tggaaaattt aaataaaaaa gttgatgatg   1320
gatttctgga catttggaca tataatgcag aattgttagt tctactggaa atgaaagga    1380 ctctggattt ccatgactca aatgtgaaga atctgtatga aaagtaaaa  agccaattaa   1440 agaataatgc caaagaaatc ggaaatggat gttttgagtt ctaccacaag tgtgacaatg   1500
aatgcatgga aagtgtaaga aatgggactt atgattatcc caaatattca gaagagtcaa   1560
agttgaacag ggaaaaggta gatggagtga aattggaatc aatggggatc tatcagattc   1620
tggcgatcta ctcaactgtc gccagttcac tggtgctttt ggtctccctg ggggcaatca   1680
gtttctggat gtgttctaat ggatctttgc agtgcagaat atgcatctga gattagaatt   1740
tcagagatat gaggaaaaac accttgtttc ctact                              1775

<210> SEQ ID NO 8
<211> LENGTH: 1413
<212> TYPE: DNA
<213> ORGANISM: Influenza virus

<400> SEQUENCE: 8
agcaaaagca ggggtttaaa atgaatccaa atcagaaaat aataaccatt ggatcaatct     60
gtctggtagt cggactaatt agcctaatat tgcaaatagg aaatataatc tcaatatgga    120
ttagccattc aattcaaact ggaagtcaaa accatactgg aatatgcaac caaaacatca    180
ttacctataa aaatagcacc tgggtaaagg acacaacttc agtgatatta accggcaatt    240
catctctttg tcccatccgt gggtgggcta tatacagcaa agacaatagc ataagaattg    300
gttccaaagg agacgttttt gtcataagag agccctttat ttcatgttct cacttggaat    360
gcaggacctt tttctgacc  caaggtgcct tactgaatga caagcattca gtgggactg     420 ttaaggacag aagcccttat agggccttaa tgagctgccc tgtcggtgaa gctccgtccc    480
cgtacaattc aagatttgaa tcggttgctt ggtcagcaag tgcatgtcat gatggcatgg    540
gctggctaac aatcggaatt tcaggtccag ataatggagc agtggctgta ttaaaataca    600
acggcataat aactgaaacc ataaaaagtt ggaggaagaa aatattgagg acacaagagt    660
ctgaatgtgc ctgtgtaaat ggttcatgtt ttactataat gactgatggc ccgagtgatg    720
ggctggcctc gtacaaaatt ttcaagatcg aaaaggggaa ggttactaaa tcaatagagt    780
tgaatgcacc taattctcac tatgaggaat gttcctgtta ccctgatacc ggcaaagtga    840
tgtgtgtgtg cagagacaat tggcatggtt cgaaccggcc atgggtgtct ttcgatcaaa    900
acctggatta tcaaatagga tacatctgca gtggggtttt cggtgacaac ccgcgtcccg    960
```

-continued

```
aagatggaac aggcagctgt ggtccagtgt atgttgatgg agcaaacgga gtaaagggat    1020
tttcatatag gtatggtaat ggtgtttgga taggaaggac caaaagtcac agttccagac    1080
atgggtttga gatgatttgg gatcctaatg gatggacaga gactgatagt aagttctctg    1140
tgaggcaaga tgttgtggca atgactgatt ggtcagggta tagcggaagt ttcgttcaac    1200
atcctgagct gacagggcta gactgtatga ggccgtgctt ctgggttgaa ttaatcaggg    1260
gacgacctaa agaaaaaaca atctggacta gtgcgagcag catttctttt tgtggcgtga    1320
atagtgatac tgtagattgg tcttggccag acggtgctga gttgccattc agcattgaca    1380
agtagtctgt tcaaaaaact ccttgtttct act                                 1413
```

<210> SEQ ID NO 9
<211> LENGTH: 31
<212> TYPE: DNA
<213> ORGANISM: Artificial Sequence
<220> FEATURE:
<223> OTHER INFORMATION: A synthetic primer

<400> SEQUENCE: 9
cacacacggt ctccgggagc gaaagcaggc a                                     31

<210> SEQ ID NO 10
<211> LENGTH: 22
<212> TYPE: DNA
<213> ORGANISM: Artificial Sequence
<220> FEATURE:
<223> OTHER INFORMATION: A synthetic primer

<400> SEQUENCE: 10
gggtttgtat ttgtgtgtca cc                                              22

<210> SEQ ID NO 11
<211> LENGTH: 24
<212> TYPE: DNA
<213> ORGANISM: Artificial Sequence
<220> FEATURE:
<223> OTHER INFORMATION: A synthetic primer

<400> SEQUENCE: 11
ccaggacact gaaatttctt tcac                                            24

<210> SEQ ID NO 12
<211> LENGTH: 35
<212> TYPE: DNA
<213> ORGANISM: Artificial Sequence
<220> FEATURE:
<223> OTHER INFORMATION: A synthetic primer

<400> SEQUENCE: 12
cacacaggtc tcctattagt agaaacaagg cattt                                35

<210> SEQ ID NO 13
<211> LENGTH: 30
<212> TYPE: DNA
<213> ORGANISM: Artificial Sequence
<220> FEATURE:
<223> OTHER INFORMATION: A synthetic primer

<400> SEQUENCE: 13
cacacaggtc tccgggagcg aaagcaggtc                                      30

<210> SEQ ID NO 14
<211> LENGTH: 30

```
<212> TYPE: DNA
<213> ORGANISM: Artificial Sequence
<220> FEATURE:
<223> OTHER INFORMATION: A synthetic primer

<400> SEQUENCE: 14
cacacacgtc tccatcatac aatcctcttg                              30

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

<400> SEQUENCE: 15
ctcctctgat ggtggcatac                                         20

<210> SEQ ID NO 16
<211> LENGTH: 36
<212> TYPE: DNA
<213> ORGANISM: Artificial Sequence
<220> FEATURE:
<223> OTHER INFORMATION: A synthetic primer

<400> SEQUENCE: 16
cacacaggtc tcctattagt agaaacaagg tcgttt                       36

<210> SEQ ID NO 17
<211> LENGTH: 31
<212> TYPE: DNA
<213> ORGANISM: Artificial Sequence
<220> FEATURE:
<223> OTHER INFORMATION: A synthetic primer

<400> SEQUENCE: 17
cacacacgtc tccgggagcg aaagcaggta c                            31

<210> SEQ ID NO 18
<211> LENGTH: 35
<212> TYPE: DNA
<213> ORGANISM: Artificial Sequence
<220> FEATURE:
<223> OTHER INFORMATION: A synthetic primer

<400> SEQUENCE: 18
cacacacgtc tcctattagt agaaacaagg tactt                        35

<210> SEQ ID NO 19
<211> LENGTH: 30
<212> TYPE: DNA
<213> ORGANISM: Artificial Sequence
<220> FEATURE:
<223> OTHER INFORMATION: A synthetic primer

<400> SEQUENCE: 19
cacacacgtc tccgggagca aaagcagggg                              30

<210> SEQ ID NO 20
<211> LENGTH: 37
<212> TYPE: DNA
<213> ORGANISM: Artificial Sequence
<220> FEATURE:
<223> OTHER INFORMATION: A synthetic primer

<400> SEQUENCE: 20
cacacacgtc tcctattagt agaaacaagg gtgtttt                      37
```

```
<210> SEQ ID NO 21
<211> LENGTH: 31
<212> TYPE: DNA
<213> ORGANISM: Artificial Sequence
<220> FEATURE:
<223> OTHER INFORMATION: A synthetic primer

<400> SEQUENCE: 21
cacacacgtc tccgggagca aaagcagggt a                                           31

<210> SEQ ID NO 22
<211> LENGTH: 38
<212> TYPE: DNA
<213> ORGANISM: Artificial Sequence
<220> FEATURE:
<223> OTHER INFORMATION: A synthetic primer

<400> SEQUENCE: 22
cacacacgtc tcctattagt agaaacaagg gtatttttt                                   38

<210> SEQ ID NO 23
<211> LENGTH: 31
<212> TYPE: DNA
<213> ORGANISM: Artificial Sequence
<220> FEATURE:
<223> OTHER INFORMATION: A synthetic primer

<400> SEQUENCE: 23
cacacaggtc tccgggagca aaagcaggag t                                           31

<210> SEQ ID NO 24
<211> LENGTH: 38
<212> TYPE: DNA
<213> ORGANISM: Artificial Sequence
<220> FEATURE:
<223> OTHER INFORMATION: A synthetic primer

<400> SEQUENCE: 24
cacacaggtc tggtattagt agaaacaagg agttttt                                     38

<210> SEQ ID NO 25
<211> LENGTH: 31
<212> TYPE: DNA
<213> ORGANISM: Artificial Sequence
<220> FEATURE:
<223> OTHER INFORMATION: A synthetic primer

<400> SEQUENCE: 25
cacacacgtc tccgggagca aaagcaggta g                                           31

<210> SEQ ID NO 26
<211> LENGTH: 38
<212> TYPE: DNA
<213> ORGANISM: Artificial Sequence
<220> FEATURE:
<223> OTHER INFORMATION: A synthetic primer

<400> SEQUENCE: 26
cacacacgtc tcctattagt agaaacaagg tagttttt                                    38

<210> SEQ ID NO 27
<211> LENGTH: 31
<212> TYPE: DNA
<213> ORGANISM: Artificial Sequence
<220> FEATURE:
<223> OTHER INFORMATION: A synthetic primer
```

```
<400> SEQUENCE: 27
cacacacgtc tccgggagca aaagcagggt g                                    31

<210> SEQ ID NO 28
<211> LENGTH: 37
<212> TYPE: DNA
<213> ORGANISM: Artificial Sequence
<220> FEATURE:
<223> OTHER INFORMATION: A synthetic primer

<400> SEQUENCE: 28
cacacacgtc tcctattagt agaaacaagg gtgtttt                              37

<210> SEQ ID NO 29
<211> LENGTH: 33
<212> TYPE: DNA
<213> ORGANISM: Artificial Sequence
<220> FEATURE:
<223> OTHER INFORMATION: A synthetic vector sequence

<400> SEQUENCE: 29
gggttattgg agacggtacc gtctcctccc ccc                                  33

<210> SEQ ID NO 30
<211> LENGTH: 33
<212> TYPE: DNA
<213> ORGANISM: Artificial Sequence
<220> FEATURE:
<223> OTHER INFORMATION: A synthetic vector sequence

<400> SEQUENCE: 30 gggggggagga gacggtaccg tctccaataa ccc                                 33

<210> SEQ ID NO 31
<211> LENGTH: 18
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(18)
<223> OTHER INFORMATION: n = A,T,C or G

<400> SEQUENCE: 31
cgtctcntat tagtagaa                                                   18

<210> SEQ ID NO 32
<211> LENGTH: 17
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(17)
<223> OTHER INFORMATION: n = A,T,C or G

<400> SEQUENCE: 32
ttttgctccc ngagacg                                                    17

<210> SEQ ID NO 33
<211> LENGTH: 17
<212> TYPE: DNA
<213> ORGANISM: Artificial Sequence
```

<220> FEATURE:
<223> OTHER INFORMATION: A synthetic vector/influenza viral cDNA sequence
<220> FEATURE:
<221> NAME/KEY: misc_feature
<222> LOCATION: (1)...(17)
<223> OTHER INFORMATION: n = A,T,C or G

<400> SEQUENCE: 33
cgtctcnggg agcaaaa 17

<210> SEQ ID NO 34
<211> LENGTH: 18
<212> TYPE: DNA
<213> ORGANISM: Artificial Sequence
<220> FEATURE:
<223> OTHER INFORMATION: A synthetic vector/influenza viral cDNA sequence
<220> FEATURE:
<221> NAME/KEY: misc_feature
<222> LOCATION: (1)...(18)
<223> OTHER INFORMATION: n = A,T,C or G

<400> SEQUENCE: 34
ttctactaat angagacg 18

<210> SEQ ID NO 35
<211> LENGTH: 11
<212> TYPE: DNA
<213> ORGANISM: Artificial Sequence
<220> FEATURE:
<223> OTHER INFORMATION: A synthetic vector/influenza viral cDNA sequence

<400> SEQUENCE: 35
tattagtaga a 11

<210> SEQ ID NO 36
<211> LENGTH: 10
<212> TYPE: DNA
<213> ORGANISM: Artificial Sequence
<220> FEATURE:
<223> OTHER INFORMATION: A synthetic vector/influenza viral cDNA sequence

<400> SEQUENCE: 36
gggagcaaaa 10

<210> SEQ ID NO 37
<211> LENGTH: 15
<212> TYPE: DNA
<213> ORGANISM: Artificial Sequence
<220> FEATURE:
<223> OTHER INFORMATION: A synthetic vector/influenza viral cDNA sequence

<400> SEQUENCE: 37
gggttattag tagaa 15

<210> SEQ ID NO 38
<211> LENGTH: 13
<212> TYPE: DNA
<213> ORGANISM: Artificial Sequence
<220> FEATURE:
<223> OTHER INFORMATION: A synthetic vector/influenza viral cDNA sequence

<400> SEQUENCE: 38
ttttgctccc ccc 13

```
<210> SEQ ID NO 39
<211> LENGTH: 13
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 39 gggggagca aaa                                                              13

<210> SEQ ID NO 40
<211> LENGTH: 15
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 40
ttctactaat aaccc                                                           15
```